(12) United States Patent
Bailey et al.

(10) Patent No.: US 10,357,496 B2
(45) Date of Patent: Jul. 23, 2019

(54) METHODS, FORMULATIONS, AND KITS FOR RAPIDLY REPLETING FOLATE LEVELS IN WOMEN

(71) Applicant: SOUTH ALABAMA MEDICAL SCIENCE FOUNDATION, Mobile, AL (US)

(72) Inventors: Steven W. Bailey, Mobile, AL (US); June E. Ayling, Mobile, AL (US)

(73) Assignee: South Alabama Medical Science Foundation, Mobile, AL (US)

(*) Notice: Subject to any disclaimer, the term of this patent is extended or adjusted under 35 U.S.C. 154(b) by 187 days.

(21) Appl. No.: 13/261,852

(22) PCT Filed: Nov. 5, 2012

(86) PCT No.: PCT/US2012/000536
§ 371 (c)(1),
(2) Date: May 5, 2014

(87) PCT Pub. No.: WO2013/066375
PCT Pub. Date: May 10, 2013

(65) Prior Publication Data
US 2014/0315853 A1 Oct. 23, 2014

Related U.S. Application Data

(60) Provisional application No. 61/628,723, filed on Nov. 5, 2011.

(51) Int. Cl.
A61K 31/519 (2006.01)
A61K 31/7052 (2006.01)
C07D 475/04 (2006.01)
A61K 31/714 (2006.01)

(52) U.S. Cl.
CPC ........ *A61K 31/519* (2013.01); *A61K 31/7052* (2013.01); *A61K 31/714* (2013.01); *C07D 475/04* (2013.01)

(58) Field of Classification Search
CPC .............. A61K 31/519; A61K 31/7052; A61K 31/714; A61K 2300/00; C07D 475/04
USPC .................................... 514/249, 52
See application file for complete search history.

(56) References Cited

U.S. PATENT DOCUMENTS 5,059,595 A * 10/1991 Le Grazie ............ A61K 31/505
424/468
6,190,693 B1 * 2/2001 Kafrissen et al. ............ 424/451
2005/0164977 A1 * 7/2005 Coelingh Bennink ......... 514/52

OTHER PUBLICATIONS

Cole et al. The normal variabilities of the menstrual cycle. Fertil Steril 91:522-527, 2009. (Year: 2009).*

* cited by examiner

Primary Examiner — Yih-Horng Shiao
(74) Attorney, Agent, or Firm — Maynard, Cooper & Gale, P.C.; Matthew Parker

(57) ABSTRACT

Disclosed are methods for rapidly repleting folate levels of a woman for whom there is reason to believe that she may be pregnant or of a woman who believes that she may soon become pregnant. One of the methods includes administering to the woman two or more repletion doses of folate, wherein each of the repletion doses comprises no less than about 2.5 micromole of folate, wherein the repletion doses are administered no more than about one day apart, and wherein the total number of repletion doses administered to the woman is 72 or fewer.

34 Claims, 5 Drawing Sheets

METHODS, FORMULATIONS, AND KITS FOR RAPIDLY REPLETING FOLATE LEVELS IN WOMEN

The present application claims the benefit of U.S. Provisional Patent Application Ser. No. 61/628,723 filed Nov. 5, 2011, which provisional patent application is hereby incorporated by reference.

FIELD OF THE INVENTION

The present invention relates, generally, to methods, formulations, and kits for rapidly repleting folate levels of women and, more particularly, to methods, formulations, and kits for rapidly repleting folate levels of a woman for whom there is reason to believe that she may be pregnant or of a woman who believes that she may soon become pregnant.

BACKGROUND OF THE INVENTION

Inadequate folate in pregnant women has been linked to a number of abnormalities of human embryonic and fetal development having major impacts on both the newborn and society.

One of the most well documented are neural tube defects ("NTD") which arise from various abnormalities of tube closure during the fourth week of pregnancy. Two main examples of NTD are spina bifida (failure of posterior closure) and anencephaly (lack of a complete brain due to failure of anterior closure) among others. Most fetuses with anencephaly are not born alive, and the rest die shortly after birth. The majority of children with spina bifida survive to become adults. However, they face many challenges among which can be hydrocephalus, Chiari II malformation, tethered spinal cord, urinary tract disorders, and learning disabilities. Many may have ambulatory problems, loss of sensation, limb deformities, and loss of muscle tone. When the malformation is located higher in the spine, the risk of multiple complications is greater. It is not unusual for patients with NTD to undergo one or more operations to alleviate these issues, such as spinal surgery and/or placement of a shunt to relieve intracranial pressure to prevent brain damage due to hydrocephalus. The average total lifetime cost of caring for a child born with spina bifida is over $500,000. There are an estimated 70,000 patients in the United States with spina bifida, and about 3,000 births each year are affected by neural tube defects. According to the March of Dimes Global Report on Birth Defects (2006), worldwide, there were 324,000 births in 2001 affected by neural tube defects, with the majority of these occurring in India and China.

Women who have had one or more NTD affected pregnancies are at about ten times higher risk of a recurrence than the general population. An especially strong risk factor is low folate intake. One indication of low folate intake would be low intake of fruits, vegetables, and fortified cereals. Moreover, polymorphisms in several folate-related genes, for example, methylenetetrahydrofolate reductase ("MTHFR"), also appear to increase risk. Starting in the early 1980's, a number of clinical trials, some randomized and placebo controlled, demonstrated that periconceptual supplementation with folic acid considerably reduces the risk of NTD. An often quoted trial of secondary prevention was performed by the Medical Research Council ("MRC") Vitamin Study Group ("Prevention of neural tube defects: results of the Medical Research Council Vitamin Study. MRC Vitamin Study Research Group," *Lancet*, 338:131-137 (1991)) in which the treatment with 4 mg/day of folic acid prevented 72% of recurrent NTD compared to the control group. Not all NTD can be prevented by folic acid. Thus, the extent of the risk reduction depends, in part, on the incidence of NTD in a given population. For example, two regions in China participated in a trial of 400 µg/d of folic acid. Before intervention, the northern and southern regions had rates of 48 and 10 NTD cases per 10,000 births, respectively. After folic acid treatment these decreased to 10 and 6 per 10,000, respectively, indicating that a greater risk reduction can be obtained with populations having higher initial risk. In countries that have adopted mandatory fortification with folic acid or in clinical trials for primary prevention of neural tube defects, the rate of neural tube affected births has been decreased to a level not less than about 4 per 10,000 births or 7 per 10,000 births and abortions. These folate non-responsive cases are considered to be an outcome of multifactorial causes of NTD.

Although a number of studies have indicated that women who are folate deficient are at increased risk for NTD, it has also been shown in a population of Irish subjects that simply having average folate levels is not fully protective; a projection of NTD risk versus red cell folate concentration indicated that the optimum level was at least 906 nmol/L. Thus, it has been considered that women who have had an affected birth may require higher than normal levels to overcome one or more barriers to full utilization of folate. The above-mentioned MTHFR polymorphism, although representing only a small portion of the population at risk, is perhaps one such barrier. The majority of risk cannot yet be attributed to any single genetic defect. In mouse models, there are now over 200 genes that, when disabled, promote neural tube defects, and some of these can be overcome by administration of folate. With regard to the level of folate needed to minimize risk for NTD, it should be noted that the folate in red cells is generally not considered to be readily exchanged with tissues. Red cell folate is thought to be an indicator of the average folate levels over the last several months since it is not subject to recent and transient increases due to dietary intake. However, it is the plasma that can supply folate to various organs. In particular, shortly after implantation, the trophoblast of the human embryo integrates with the endometrium of the mother to provide a path for nutrient uptake from the plasma. This initial system will not develop into a complete placenta until well after neural tube closure. From the standpoint of the developing embryo, what is important is not necessarily the red cell folate concentration, but rather the level of plasma folate averaged over each day. In the early stages of embryonic development the degeneration of decidual cells in the endometrium shortly after implantation also can supply nutrients. Again, however, the nutrient content (such as folate) of such cells is more likely to reflect recent plasma concentrations than would red cell folate. Since a dose of folate produces a transient increase in the blood that clears over several hours, a fasting plasma sample that is remote from the last intake of folate represents a level close to the minimum for the day.

Several trials (both primary and secondary) have examined the reduction of risk for NTD at various doses of folic acid. The group treated with 400 µg/d folic acid in the trial northern and southern China reduced incidence of NTD to a level about as low as seen in other studies at higher doses. From this, many have concluded that long term supplementation with 400 µg/d is sufficient to almost fully remove the folate dependent risk for NTD. In addition, several studies have examined the folate levels achieved with long term folic acid supplementation. The plateau value of plasma folate achieved after many months of consumption of 400 µg/d is between 35 nM to more typically near 50 nM.

The current Recommended Daily Intake ("RDI") in the U.S. for folate is 400 µg/d for the general population and 800 µg/d for pregnant and lactating women. Several public health agencies advise that all women of child bearing age consume a daily supplement containing 400 µg of folic acid regardless of specific plans for becoming pregnant. This is based on the understanding that neural tube closure is typically complete by about 28 days after conception. A study of the rate at which 400 µg/d of folic acid or 5-methyltetrahydrofolate increases folate levels when administered to young women showed that a plateau was reached in the plasma only after 12 weeks. Another study with a daily dose of 800 µg indicated that red cell concentrations could be elevated to what has been considered to be the fully protective level of 906 nM only after 4.2±3.5 weeks of treatment (Daly et al., "Folate Levels and Neural Tube Defects. Implications for Prevention," *JAMA*, 274(21):1698-1702 (1995)). A report by Nguyen et al, "Steady State Folate Concentrations Achieved with 5 Compared with 1.1 Mg Folic Acid Supplementation Among Women of Childbearing Age," Am. J. Clin. Nut., 89:844-852 (2009), showed that a group of women, who at baseline were already well above a red cell folate level of 1,000 nM, could be made even more replete by 2 weeks when given 1.1 or 5 mg/d of folic acid. The Upper Tolerable Limit for folic acid has been set to be 1.0 mg based primarily on the potential adverse interaction of high folate levels concurrent with undiagnosed vitamin B12 deficiency. Thus, it is widely believed that supplementation with folic acid should start at least several months prior to planning a pregnancy. However, only about one third of women of child bearing age in the U.S. consume supplements containing folic acid daily. Moreover, about one half of pregnancies are unplanned.

As a result, many countries have established mandatory fortification with folic acid based largely on the initial experience in the United States. Folic acid is typically added to a widely consumed grain, such as wheat, to expose the population to an average level based on the typical pattern of intake. This approach has been shown to increase the average folate levels of the population while at the same time decreasing the risk for NTD. Despite the success of these fortification programs, several groups remain unprotected. First, many countries, for example those within Europe, have not introduced mandatory fortification. Part of the debate preventing implementation is that mandatory fortification exposes the entire population to folic acid when the target is primarily only women of child bearing age. High folic acid intake by those who are vitamin B12 deficient, e.g., especially the elderly, can exacerbate neurologic damage. In several countries, even voluntary fortification, such as of breakfast cereals, is either minimal or banned. People in these areas must rely almost exclusively on the endogenous natural folate in the food they eat, and can have relatively low blood folate levels if not consuming supplements. Second, even in the countries having folic acid fortification, such as the U.S., there are subpopulations of women of child bearing age who have well below average folate levels. Such women would not be considered folate deficient according to criteria related to minimizing anemia or elevated homocysteine. However, as mentioned above, higher than average folate levels is required to fully decrease the risk of NTD affected births in those who are susceptible. According to the currently accepted thinking, once a woman has been determined to be pregnant and also to have low blood folate levels, it is considered too late to initiate administration of folic acid to meaningfully decrease the chance of having an NTD affected birth. She would, nonetheless, typically be prescribed a folic acid containing prenatal supplement to avert other problems later in pregnancy.

Inadequate folate in pregnant women has also been linked to congenital heart defects. Congenital heart defects, which affect almost 1% of live births, have a substantial impact on the viability and health of the newborn. It is one of the most common birth defects, affecting about 35,000 children a year in the United States alone, and more than 1 million worldwide. Defects of the ventricular outflow tract are a major contributor to cardiac conotruncal anomalies. It has been found that migration and integration of cells from the neural crest is essential for septation of the outflow tract and development of the aortic arch arteries. In humans migration of the cardiac neural crest cells commences as the neural tube is closing, and then enter the aortic arches and nascent outflow tracts between 32 to 37 days. By about 8 weeks after conception the outflow tract and ventricular septation is complete.

A number of studies have indicated a protective role for folate in preventing congenital heart defects, and a recent review concluded that periconceptional use of folic acid was associated with 20% decrease in the prevalence of heart defects. Mandatory fortification of flour with folic acid in Canada starting in 1998 has been observed to be related to a sharp decrease in heart defects in Quebec Province.

Similar to the heart, much of the prechordal plate that eventually gives rise to the mouth also arises from migration of neural crest cells. The lip normally closes by 35 to 40 days after conception, and the palate by 7 to 10 weeks. Orofacial clefts are common birth defects which can be classified as improper closure of the lip or palate or both. In the United States, over 4,200 and 2,600 babies with cleft lip/palate and cleft lip only are born each year, respectively. A smaller number of births are affected by orofacial clefts in conjunction with other defects (syndromic clefts).

The precise knowledge of the effect of periconceptual folic acid administration on orofacial clefts is limited by a deficiency of randomized controlled trials. However, several intervention trials have indicated a reduction in risk for recurrence, especially of cleft lip/palate. A meta-analysis of these results suggested about a two thirds reduction in recurrence. A relative risk reduction of 0.25 has been reported for non-syndromic cleft lip/palate in a study in northern China.

For each of the above heart, lip/palate, and especially neural tube birth defects, there is evidence that administration of folic acid can reduce the risk of occurrence or reoccurrence. The current and widespread understanding is that this folic acid must be given sufficiently in advance of pregnancy by many weeks if not several months to be effective.

Adequate folate during pregnancy has been linked to several other conditions.

For example, observational studies and clinical trials have indicated that folate intake during pregnancy is associated with higher birthweight. The risk of morbidity and death in infancy is increased by low birthweight. Folate levels can also influence methylation patterns, alteration of which has also recently been shown to be associated with birthweight.

A relationship has been observed between increased risk for autism and a interpregnancy interval shorter than 24 months. For example, a child born within 12 months of the previous sibling was over three times as likely to be diagnosed with autism spectrum disorder than the most spaced (>3 years) group. It was suggested that folate depletion of the mother during a given pregnancy might carry over to the next if not adequately spaced. More recently, a mother's use of prenatal vitamins prior to pregnancy or within the first month of pregnancy has been correlated with decreased risk of autism. This correlation was especially strong in women having the MTHFR TT or cystathionine β-synthase (GT or TT) genotypes. Although the hypothesis that the mother's folate levels is related to risk of autism in her offspring remains to be confirmed, the current thinking is that this may be a factor in decreasing the risk for autism.

In view of the above discussion, there is a great unmet need for a way to decrease the occurrence of birth defects among women who do not have optimal folate levels and to reduce the risk of NTD and other birth defects and disorders/pathologies among women who are found to be pregnant while possibly having inadequate plasma folate and/or other risk factors. The present invention, at least in part, is meant to address these needs.

SUMMARY OF THE INVENTION

The present invention relates to methods for rapidly repleting folate levels of a woman for whom there is reason to believe that she may be pregnant or of a woman who believes that she may soon become pregnant. The methods include administering to the woman two or more repletion doses of folate, wherein each of the repletion doses comprises no less than about 2.5 micromole of folate, wherein the repletion doses are administered no more than about one day apart, and wherein the total number of repletion doses administered to the woman is 72 or fewer.

The present invention also relates to methods for rapidly repleting folate levels of a woman for whom there is reason to believe that she may be pregnant or of a woman who believes that she may soon become pregnant. The methods include administering folate to the woman during a repletion phase, wherein the total amount of folate administered to the woman per day during the repletion phase is greater than about 10 micromole and no greater than about 200 micromole and wherein the repletion phase is carried out for no more than about 12 days.

The present invention also relates to methods for rapidly repleting folate levels of a woman for whom there is reason to believe that she may be pregnant or of a woman who believes that she may soon become pregnant. The methods include administering folate to the woman during a repletion phase, wherein the amount of folate administered per dose and the number of doses administered per day are selected such that the woman's minimum plasma folate level does not fall below 35 nM and wherein the repletion phase is carried out for no more than about 12 days.

The present invention also relates to methods for rapidly repleting folate levels of a woman for whom there is reason to believe that she may be pregnant or of a woman who believes that she may soon become pregnant. The methods include administering to the woman two or more repletion doses comprising reduced folate and, optionally, folic acid, wherein each of the repletion doses comprises no less than about 2.5 micromole of reduced folate and optional folic acid and wherein the repletion doses are administered no more than about one day apart.

The present invention also relates to methods for rapidly repleting folate levels of a woman for whom there is reason to believe that she may be pregnant or of a woman who believes that she may soon become pregnant. The methods include administering reduced folate and, optionally, folic acid to the woman during a repletion phase, wherein the total amount of reduced folate and optional folic acid administered to the woman per day during the repletion phase is greater than about 10 micromole and no greater than about 200 micromole.

The present invention also relates to a sustained-release folate formulation. The sustained-release folate formulation includes a reduced folate and, optionally, folic acid incorporated in a matrix effective to release from about 4 to about 200 micromoles of the reduced folate and optional folic acid over a period of from about 4 hours to about 2 days, wherein said sustained-release formulation is suitable for administration to a woman for whom there is reason to believe that she may be pregnant or of a woman who believes that she may soon become pregnant.

The present invention also relates to a kit. The kit includes a pregnancy test device and a repletion dose of folate comprising no less than about 2.5 micromole of folate.

BRIEF DESCRIPTION OF THE DRAWINGS

FIG. 5 also shows the rate of increase of total serum folate with folic acid administration for a subject whose serum total folate never reached a concentration higher than 32 nM (open circles, thin solid line).

DETAILED DESCRIPTION OF THE INVENTION

Figure 1:
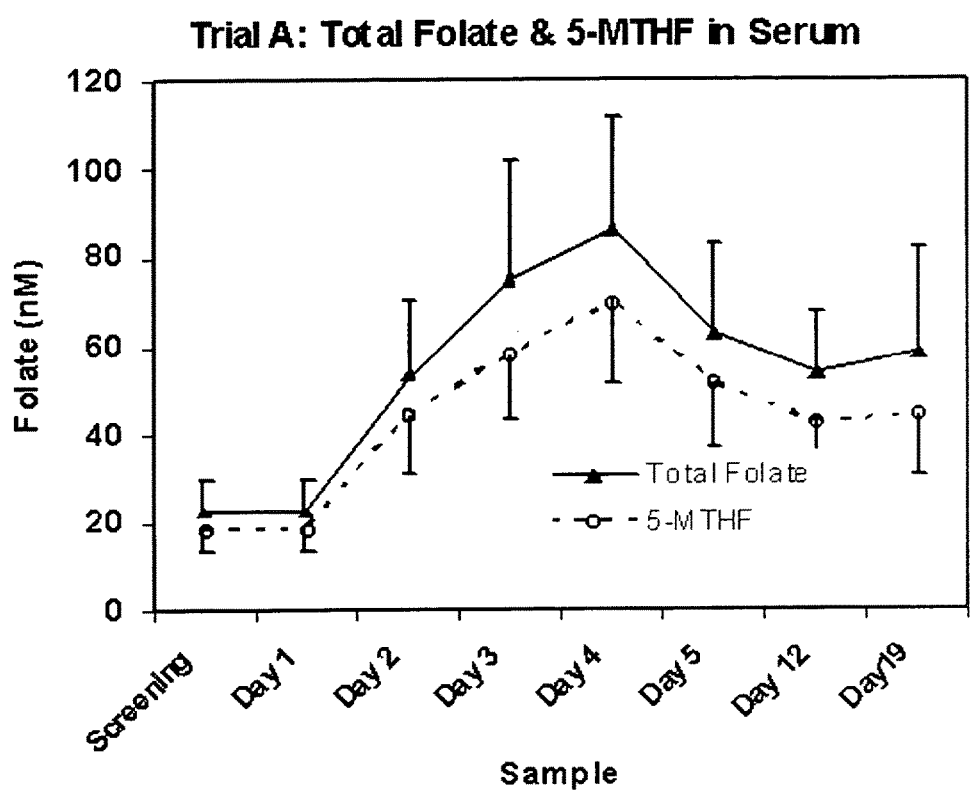
FIG. 1 is a graph showing the results of a study (Trial A) of the rate of increase of serum folate with 5-methyltetrahydrofolate ("5-MTHF") administration. The solid line represents total serum folate, and the dotted line represents the 5-MTHF component of the total serum folate.

The present invention relates to a method for rapidly repleting folate levels of a woman for whom there is reason to believe that she may be pregnant or of a woman who believes that she may soon become pregnant. In one aspect of the present invention, the method includes administering to the woman two or more repletion doses of folate, wherein each of the repletion doses comprises no less than about 2.5 micromole of folate, wherein the repletion doses are administered no more than about one day apart, and wherein the total number of repletion doses administered to the woman is 72 or fewer. In another aspect of the present invention, the method includes administering folate to the woman during a repletion phase, wherein the total amount of folate administered to the woman per day during the repletion phase is greater than about 10 micromole and no greater than about 200 micromole and wherein the repletion phase is carried out for no more than about 12 days. In yet another aspect of the present invention, the method includes administering folate to the woman during a repletion phase, wherein the amount of folate administered per dose and the number of doses administered per day are selected such that the woman's minimum plasma folate level does not fall below 35 nM and wherein the repletion phase is carried out for no more than about 12 days. In still another aspect of the present invention, the method includes administering to the woman two or more repletion doses comprising reduced folate and, optionally, folic acid, wherein each of the repletion doses comprises no less than about 2.5 micromole of reduced folate and optional folic acid and wherein the repletion doses are administered no more than about one day apart. In yet another aspect of the present invention, the method includes administering reduced folate and, optionally, folic acid to the woman during a repletion phase, wherein the total amount of reduced folate and optional folic acid administered to the woman per day during the repletion phase is greater than about 10 micromole and no greater than about 200 micromole.

As used herein, "for whom there is reason to believe that she may be pregnant" is meant to include women of childbearing age or capable of becoming pregnant who are in fact be pregnant as well as those who are in fact be not pregnant. The woman can be one who herself has reason to believe that she may be pregnant; or, alternatively, the woman can be one who has no reason to herself to believe that she may be pregnant but for whom another person (e.g., her physician) has reason to believe that she may be pregnant. By way of illustration, the woman can have reason to believe that she may be pregnant as the result of having had sexual intercourse, having had unprotected sexual intercourse, having missed her menses, having a positive in-home pregnancy test, and/or having a positive point-of-care pregnancy test. These and other reasons that can result in a woman believing that she may have recently become pregnant are discussed further below.

The primary change noticed first by many women is a missed or abnormal period, an observation that can be confused by a slight implantation bleeding (spotting, which occurs between six to 12 days after conception). However, there are several other signs and symptoms of possible pregnancy such as basal body temp; tender, sore, tingly or swollen breasts; fatigue; headaches; mood swings; and milky white vaginal discharge.

The most widely used method to detect pregnancy is the measurement of human chorionic gonadotropin ("hCG") in serum or urine. There are several variants of hCG such as the intact form, the beta subunit, the nicked form, the nicked subunit, and the core beta fragment. In addition, there is a hyperglycosylated form that is especially abundant early in pregnancy. Tests can be qualitative or quantitative, the latter being more sensitive, and can vary in the specific forms that are detected. The quantitative analysis of hCG in serum has a detection limit of about 1 IU/L, depending on the manufacturer, variant being examined, and the assay platform. Non-pregnant premenopausal females have serum levels below ~5 IU/mL, but, after embryonic implantation, hCG begins to double every 1.5 to 3 days. Pregnancy is clearly indicated by a value greater than 25 IU/L. Some, but not all, consider values between 6 to 25 IU/L to be somewhat less certain due to the possible transient hCG increases resulting from an early pregnancy loss or high background due to malignancy. The quantitative serum test can detect the rise in hCG typically between 6 to 12 days after ovulation. In one study, among women where hCG was first detected later than 12 days after ovulation, no long term pregnancies resulted, most likely a result of early pregnancy loss. The quantitative serum hCG test is a laboratory procedure, which has a turnaround time of typically between about an hour to one day.

Qualitative urine tests are available as over-the-counter ("OTC") products for home testing and point-of-care ("POC") products for rapid testing in doctors' offices. These have a broad range of claimed sensitivity from between about 15 to over 50 IU/L, although independent testing indicates that some brands are better and others worse than claimed. Urine that is not overly diluted with high fluid intake has hCG levels somewhat similar to those of serum. However, highly diluted urine can lead to a false negative reading. Some laboratories measure hCG in urine in conjunction with correction for specific gravity or creatinine. Devices from various OTC device manufactures have different profiles for detection of the variant forms of hCG. Moreover, the sensitivity of a given device can vary among individuals. Still, when the instructions are correctly followed, the most sensitive OTC urine tests can detect pregnancy as early as 1 to 3 days after implantation. Implantation of the blastocyst into the endometrium begins toward the end of the first week after conception and is generally complete by the end of the second week. The average length of the luteal phase (from ovulation to menstruation) is about 13 days, and is more consistent for a given woman and also between women than the length of the follicular phase. Therefore, although some OTC tests with poor sensitivity have less than a 50% chance of detecting pregnancy on the day of a missed menses, the most sensitive brands can detect pregnancy in some women several days prior to the expected date of menstruation.

One of the earliest indications of fertilization is the increase of early pregnancy factor ("EPF") in maternal blood or cervical mucus. There are data suggesting that EPF is an extracellular form of Hsp10. It can be found in a woman's serum within 24 to 48 hours of fertilization. Since not all blastocysts implant subsequent to fertilization, a positive test does not always indicate that a viable embryo will ensue. Still, a positive test provides a "reason to believe that the woman may have recently become pregnant" and can provide an indication that folate repletion treatment according to the present invention should be initiated. Subsequent implantation can be then confirmed by a test for hCG in blood or urine. Although not commercially available either as an OTC product or for routine analysis by physicians, with further validation EPF has the potential to become the earliest indicator of pregnancy yet studied. Other proteins and hormones occur in response to pregnancy, and are being investigated as potential additional diagnostic indicators of progression and viability. Estradiol and progesterone increase quickly after ovarian stimulation by hCG. Relaxin, another ovarian product, is found in the serum nearly as soon as hCG itself. The pattern of variation of the estrogen and progesterone metabolites estrone-3-glucuronide and pregnanediol-3-glucuronide can also provide a further indication of the likelihood of pregnancy.

In addition to various indicators of pregnancy, some women choose to monitor their fertility via an ovulation test using an OTC product that measures lutenizing hormone. Some such products also incorporate a test for estrone-3-glucuronide as an additional indicator of fertility. Having the knowledge of when ovulation has occurred allows prediction of the timing of the next menses. This is more accurate than projection from the last menstrual period since the luteal phase is usually more consistent than the length of the overall cycle. A woman who is actively trying to conceive, therefore, has several tools by which to determine if at least implantation has occurred even at a date somewhat earlier than that of the missed menstrual period itself.

As used herein, "a woman who has reason to believe that she may soon become pregnant" is meant to include women of child-bearing age or capable of becoming pregnant. The woman can have reason to believe that she may soon become pregnant as a result of, for example, the woman's contemplating having sexual intercourse, the woman's contemplating having unprotected sexual intercourse, the woman's contemplating discontinuing the use of birth control, the woman's having discontinued the use of birth control, the woman's contemplating the use of fertility aids or drugs, the woman's use of fertility aids or drugs, the woman's contemplating the use of natural family planning methods to enhance fertility, the woman's use of natural family planning methods to enhance fertility, the woman's contemplating undergoing an intrauterine insemination procedure, the woman's contemplating undergoing an in vitro fertilization procedure, the woman's having begun an in vitro fertilization procedure, and the like.

In those cases where there is reason to believe that the woman may be pregnant, the a first repletion dose of folate should be administered as soon as possible or practical after becoming aware that the woman may be pregnant (e.g., after the woman having a positive pregnancy test). By way of illustration, the first repletion dose of folate can be administered within 22 days, within 21 days, within 20 days, within 19 days, within 18 days, within 17 days, within 16 days, within 15 days, within 14 days, within 13 days, within 12 days, within 11 days, within 10 days, within 9 days, within 8 days, within 7 days, within 6 days, within 5 days, within 4 days, within 48 hours, within 36 hours, within 24 hours, within 12 hours, within 8 hours, within 6 hours, within 4 hours, within 1 hour, within 30 minutes) of becoming aware that the woman may be pregnant (e.g., of the woman having a positive pregnancy test). For example, the first repletion dose of folate can be administered within 24 hours of the woman having a positive pregnancy test. This first repletion dose of folate can be packaged with the pregnancy test device, or not. It will be appreciated that, in order to optimize the effectiveness of rapid repletion with respect to prevention of neural tube defects, it is important to initiate this repletion before day 28 after conception. Several methods are available for estimating this optimal timing depending on the way or ways by which pregnancy is detected. Using a positive high sensitivity hCG test, for example, a woman would have at most about 22 days within which to consume the first dose of the repletion regime. Considering the ranges that have been reported for the luteal phase, women should also start the first dose within 22 days of missing a menstrual period. Of course, this will vary from woman to woman, depending, for example, on the duration of a particular woman's luteal phase (the length of time from ovulation to the beginning of menstruation). By way of illustration, if the first repletion dose were administered 19 days after a missed menses, there is a 2.5% chance that the first dose is being administered about one day prior to neural tube closure being complete; if the first repletion dose were administered 14 days after a missed menses, there is a 50% chance that the first dose is being administered about one day prior to neural tube closure being complete; and if the first repletion dose were administered 7 days after a missed menses, there is a 97.5% chance that the first dose is being administered about one day prior to neural tube closure being complete. It would be better to commence the repletion phase prior to the time when neural tube closure begins instead of when it ends. For example, if the first repletion dose were administered 13 days after a missed menses, there is about a 2.5% chance that the first dose is being administered before neural tube closure begins; if the first repletion dose were administered 8 days after a missed menses, there is about a 50% chance that the first dose is being administered before neural tube closure begins; and if the first repletion dose were administered 1 day after a missed menses, there is about a 97.5% chance that the first dose is being is being administered before neural tube closure begins. A woman who is monitoring her fertility, for example, by lutenizing hormone test device or by maximum cervical mucus discharge, can use this additional information to calculate 28 days from the window of ovulation. A woman who has used a fertility test device on earlier occasions can use this to calculate her own particular luteal length. This length in days can be subtracted from 28 to give her time remaining after a missed menstrual period within which to initiate repletion. Rapid repletion should be started as soon as possible within these intervals but, preferably, as soon as possible or practical after becoming aware that the woman may be pregnant (e.g., after the woman has a positive pregnancy test or a missed menses). Initiation of rapid repletion subsequent to 28 days post conception can still be of benefit in decreasing the risk of cleft lip/palate, heart defects, and other birth disorders.

The woman can be one who is established as having inadequate folate levels for the purpose of minimizing risk for birth defects, or the woman can be one who is not established as having inadequate folate levels for the purpose of minimizing risk for birth defects. Establishing whether or not a particular woman has inadequate folate levels can be carried out, for example, by measuring the woman's fasting plasma folate level, by measuring the woman's red cell folate level, or both. Methods for measuring fasting plasma folate level and for measuring red cell folate level are described, for example, in Quinlivan et al., "The Analysis of Folate and its Metabolic Precursors in Biological Samples," *Anal Biochem.*, 348(2):163-184 (2006); Pfeiffer et al., "Folate Analytical Methodology," pp. 517-574 in *Folate in Health and Disease, Second Edition*, Bailey, ed., CRC Press (2010); and Pfeiffer et al., "Comparison of Serum and Red Blood Cell Folate Microbiologic Assays for National Population Surveys," *J. Nutr.*, 141(7): 1402-1409 (2011), which are hereby incorporated by reference. For the purposes of the present invention, a woman having a measured fasting plasma level at or below 35 nM and/or having a measured red cell folate level at or below 906 nM is to be considered as being one who is established as having inadequate folate levels. Note that "plasma folate level", as used here and elsewhere in the present application, refers to the total plasma folate level, i.e., the total of all of the folates (folic acid plus all of the reduced folates) in the plasma as measured by an Immulite 2000 competitive binding assay, unless otherwise specified.

The woman can be one who is established as having adequate folate levels, or the woman can be one who is not established as having adequate folate levels. A woman having a measured fasting plasma level above 35 nM or a measured red cell folate level above 906 nM is to be considered as being one who is established as having adequate folate levels.

The woman can be one who has one or more additional risk factors and is, therefore, at increased risk for embryonic and fetal development abnormalities associated with poor folate levels, such as increased risk for NTD, increased risk for congenital heart defects, increased risk for lip/palate defects, increased risk for low birthweight, and/or increased risk for autism; or, alternatively, the woman can be one who does not have any such additional risk factors. Examples of such additional risk factors are discussed below.

Illustratively, besides folate deficiency, there are other factors that increase the risk of a neural tube affected birth: a previous affected pregnancy, family history of NTD, consanguineous parents, obesity, maternal insulin-dependent diabetes, history of still births, high body temperature due to fever or hot baths early in pregnancy, taking antiseizure medications or antifolate chemotherapy agents, use of diuretics, periconceptual diarrhea, and high plasma copper levels. Gastric bypass and use of oral contraceptives, maternal age greater than 35, parity, smoking, alcohol consumption, pesticide exposure, ingestion of fumonisins, and working in certain occupations have been discussed as risk factors. Exposure of either parent to radiation, solvents, pesticides, and mercury may also increase risk of an NTD birth by the couple.

Epileptic patients who consume antiseizure medications such as valproic acid (e.g. DEPAKOTE) and carbamazepine have been found to be at increased risk for NTD. Such drugs are also used to treat psychological disorders such as bipolar disorder. In this regard, it should be noted that there are a few reports that high doses of folic acid administered intravenously provoke seizures in those with epilepsy. Nonetheless, folic acid supplementation has been recommended, for example, by the American Academy of Neurology, for female patients taking antiseizure drugs.

Due to the increased risk for NTD which has been observed in those with variants of several genes in addition to the "thermolabile" (677C>T) variant of the MTHFR gene, it has been proposed that a significant part of neural tube defects are related to the lack of full ability to perform biochemical methylation reactions, of which there are many important examples. MTHFR is responsible for producing 5-methyl-tetrahydrofolic acid ("5-methyl-THF") from 5,10-methylene-tetrahydrofolic acid ("5,10-methylene-THF"). As discussed further hereinbelow, in one aspect of the present invention, high plasma concentrations of 5-methyl-THF can be established by consuming moderate oral doses of tetrahydrofolic acid ("THF") or other one-carbon derivatives of THF, such as 5-methyl-THF, and, thus, without intending to be bound by theory, one potential additional advantage of administering 5-methyl-THF (or THF or other one-carbon derivatives of THF) would be to help overcome this metabolic block in this subpopulation of women. Other single nucleotide polymorphisms have been identified as risk factors or as potential risk factors for NTD in humans. These include, among others, the leptin receptor, the platelet derived growth factor-alpha, and the major A allele of the Brachury T-box transcription protein. Catechol-O-methyltransferase, the ATP binding cassette ("ABC") transporter-G2, breast cancer tumor suppressors gene (BRCA1), DNA methyltransferase-3b, and the morphogen sonic hedgehog, some of which when deficient in mice cause NTD, have also been proposed as candidate genes conferring risk for human NTD. Evidence for the influence on risk in various populations has been presented for glutamate carboxypeptidase II, gamma-glutamyl hydrolase, methionine synthase reductase, and several others as listed, for example, in Carter et al., "Evaluation of 64 Candidate Single Nucleotide Polymorphisms as Risk Factors for Neural Tube-Defects in a Large Irish Study Population," *Am. J. Med. Genet. A.*, 155A(1): 14-21 (2011), which is hereby incorporated by reference. Specifically within cases having meningomyelocele, not only have variants of the SLC19A1 gene been found to be associated, but also variants in the FOLR2 and FOLR3 genes. Not all of the genes identified as risk factors for NTD are directly involved in folate metabolism. Nonetheless, the expression or activity of some may be modified by S-adenosylmethionine dependent methylation reactions, which in turn require an adequate supply of methionine (the product of homocysteine remethylation by 5-methyl-THF). Moreover as stated above, not all risk for NTD can be alleviated by high folate levels before pregnancy. Therefore, it is not yet certain which genetic variants contribute to the folate independent NTD risk.

Women suffering from such risk factors in addition to having inadequate folate levels may be particularly susceptible to having NTD-affected births, and, for at least this reason, such women may be particularly benefited by the rapid repletion methods of the present invention. It will also be appreciated, however, that a woman having one or more of these or other additional risk factors for NTD would be benefited by the rapid repletion methods of the present invention, irrespective of whether or not the woman has adequate folate levels.

By way of further illustration, besides folate deficiency, several factors have been reported to increase the risk for congenital heart defects. Among these are maternal viral infection (such as with rubella), alcohol or cocaine use in pregnancy, taking anti-seizure medications, the acne medication isotretinoin, antifolate medications (e.g., trimethoprim-sulfonamide), obesity, diabetes, and several genetic polymorphisms (e.g., methylenetetrahydrofolate reductase, betaine homocysteine methyl transferase (in obese women), transcobalamin II (in women who smoke or consume alcohol), and the transcription factor ISL1.

As yet further illustration, besides folate deficiency, additional risk factors for orofacial clefts include maternal smoking, alcohol use, and illness and the use of certain drugs (e.g. corticosteroids, folate antagonists, and some anti-seizure medications). Those of Asian and Native American ancestry are more prone to orofacial cleft defects than are Caucasians or African Americans. Moreover, the risk of orofacial clefts is greater if either or especially both parents themselves are affected, or if they have already had a child with a cleft defect.

As still further illustration, evidence has been reported for increased risk for cleft lip/palate associated (to a different extent depending on the population) with single nucleotide polymorphisms in nitric oxide synthase 3, thymidylate synthase, methylenetetrahydrofolate reductase in non-Hispanic Caucasians, and methionine synthase, betaine homocysteine methyl transferase 2, methenyl-tetrahydrofolate synthetase, and SLC19A1 (reduced folate carrier protein 1) in a Hispanic population. FGF12 (a fibroblast growth factor) and IRF6 (an interferon regulatory factor), myosin heavy chain 9, MSX1 (muscle segment homeobox gene 1, HOX7), glutathione S-transferases (when combined with smoking), and N-acetyl-transferase 1 (when in combination with low folate intake) have also been reported to be associated with cleft lip/palate, whereas connexin 43 and vinculin have been tied to non-syndromic cleft lip only. Poor maternal zinc status has been reported to be a risk factor for oral clefts in some populations. In addition, biotin deficiency in mice increases the risk for cleft palate, and there is some evidence that low biotin status in humans may also be related to this defect.

With regard to the risk of low birthweight, additional risk factors include having previously had a low birthweight pregnancy.

With regard to the risk of autism, additional risk factors include an interpregnancy interval shorter than 24 months and, especially, an interpregnancy interval shorter than 3 months.

As mentioned above with regard to the additional risk factors for NTD, a woman having one or more of these or other additional risk factors for congenital heart defects, orofacial cleft defects, cleft lip/palate defects, low birthweight, and autism may be benefited by the rapid repletion methods of the present invention, irrespective of whether or not the woman has adequate folate levels. Women who have inadequate folate levels and, in addition, who have one or more of such additional risk factors may be particularly benefited by the rapid repletion methods of the present invention.

By way of illustration, the woman can be one who has previously had one or more pregnancies affected by NTD or by cleft lip/palate defects; or the woman can be one who has not previously had a pregnancy affected by NTD or by cleft lip/palate defects. By way of further illustration, the woman can be one who has previously had one or more pregnancies affected by NTD, by cleft lip/palate defects, or by heart defects; or the woman can be one who has not previously had a pregnancy affected by NTD, by cleft lip/palate defects, or by heart defects.

As indicated above, the methods of the present invention relate to "rapidly repleting folate levels" of a woman. As used herein, "rapidly repleting" refers to repletion that occurs more quickly than would be achieved using conventional prenatal products (e.g., using 800 µg/d of folic acid). Illustratively, "rapidly repleting" is meant to include repletion that occurs in about 12 days or less, in about 7 days or less, in about 4 days or less, in about 3 days or less, in about 2 days or less, in about 36 hours or less, and/or in about 24 hours or less.

"Repleting" as used herein in the context of "folate levels", refers to increasing or optimizing the minimum fasting plasma folate level of the woman. It will be appreciated that rapid repletion may have several effects. One of these is the transient elevation of the woman's plasma folate typically starting within about 30 minutes of each dose (somewhat later with sustained release formulations). Plasma folate typically then reaches a maximum concentration between one and two hours, and then falls (except with sustained release formulations). Using, for example, the doses specified herein, during this transient elevation of the woman's plasma, the developing embryo will be supplied with adequate folate even though the mother's own tissue levels may be low. A second effect of the folate doses used during the repletion phase is believed to be the elevation of the mother's tissue folate levels. It will be appreciated that the goals of the repletion phase are multiple, and include quickly providing a minimum level of folate to the early embryo. In addition, it is believed that the repletion phase also elevates the mother's tissue folate to the point where plasma folate levels can be kept at optimal levels after shifting the woman to daily administration of folate dose typical of those used in the prenatal period either alone or in a multivitamin preparation containing a folate.

Among the discoveries of the present invention is the unexpected finding that certain folate repletion dosing schedules can rapidly elevate (within a few days or even hours) plasma folate in a manner such that the folate needs of the developing embryo are continuously satisfied. Moreover, an additional discovery is of such folate dosing schedules that allow maintenance of plasma folate optimal for embryonic development upon subsequent use of typical folate containing prenatal formulations. Such dosing schedules were previously unknown or envisioned, particularly in women for whom there is reason to believe that they are pregnant.

As discussed above, in certain aspects of the present invention, the method includes administering to the woman two or more repletion doses of folate, wherein each of the repletion doses comprises no less than about 2.5 micromole of folate, wherein the repletion doses are administered no more than about one day apart, and wherein the total number of repletion doses administered to the woman is 72 or fewer. In certain embodiments, the method further comprises, subsequent to administration of the repletion doses, administering to the woman maintenance doses of folate at a daily dosage of greater than about 0.4 micromole and less than the daily repletion dose.

As used herein, "repletion doses" refer to the relatively high doses of folate that are administered to rapidly replete the woman's folate levels and are to be distinguished from "maintenance doses", which refer to the relatively low doses of folate that are, in certain embodiments, administered to maintain the woman's folate levels once it has been made replete by administration of the repletion doses.

The folate that is administered can be folic acid or, it can be a reduced folate.

Reduced folates can be administered as their natural isomers: (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives thereof. The aforementioned natural isomers can be administered in combination with a corresponding non-natural isomer ((6R)-tetrahydrofolic acid, 5-methyl-(6R)-tetrahydrofolic acid, 5-formyl-(6R)-tetrahydrofolic acid, 10-formyl-(6S)-tetrahydrofolic acid, 5,10-methylene-(6S)-tetrahydrofolic acid, 5,10-methenyl-(6S)-tetrahydrofolic acid, 5-formimino-(6R)-tetrahydrofolic acid, and polyglutamyl derivatives thereof), or they can be administered alone (i.e., substantially free from the corresponding non-natural isomer). Where the natural isomers are administered in combination with a corresponding non-natural isomer, the ratio of natural isomer to non-natural isomer can be, for example, greater than 60:40, greater than 70:30, greater than 80:20, greater than 90:10, greater than 95:5, greater than 97:3, greater than 98:2, greater than 99:1, etc. For example, suitable reduced folates include substantially chirally pure (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives thereof. As used herein, "substantially chirally pure" is meant to include mixtures having greater than 90% chiral purity (i.e., mixtures of a natural isomer and its corresponding non-natural isomer where the ratio of natural isomer to non-natural isomer is greater than 90:10). By way of further illustration, suitable reduced folates include racemic tetrahydrofolic acid, racemic 5-methyl-tetrahydrofolic acid, racemic 5-formyl-tetrahydrofolic acid, racemic 10-formyl-tetrahydrofolic acid, racemic 5,10-methylene-tetrahydrofolic acid, racemic 5,10-methenyl-tetrahydrofolic acid, racemic 5-formimino-tetrahydrofolic acid, and polyglutamyl derivatives thereof.

As indicated above, the folates can be administered in combination (e.g., a mixture of 5-formyl-tetrahydrofolic acid and 5-methyl-tetrahydrofolic acid; a mixture of folic acid and 5-methyl-tetrahydrofolic acid; a mixture of folic acid, 5-formyl-tetrahydrofolic acid, and 5-methyl-tetrahydrofolic acid; etc.), and "folate" is meant to include such mixtures. "Folate" is also meant to include polyglutamyl derivatives.

The folic acid and reduced folates can be in either in the form of a free acid or in the form of a salt, and "folate", as used herein, is also meant to encompass both the free acid and salt forms, as well as free acid and salt forms which contain water of crystallization or which are otherwise hydrated. Examples of suitable salt forms include hydrochloride, sodium, potassium, and magnesium salts. As yet another example, the reduced folate can be in the form of a calcium salt. The salt form and crystal structure of the reduced folate somewhat affects the reduced folate's stability and solubility, and this can be optimized depending on the needs for a particular formulation. Suitable salt forms also include those in which the counter ion is an organic amine base. The pH of the final composition can also be optimized according to the stability properties of the particular reduced folate used and the other components present in the formulation (if any), as is well understood in the arts of nutrient processing and folate compounds.

The folate can be administered alone or in a pharmaceutical, supplement, or other composition containing, in addition to the reduced folate, one or more other components. Examples of suitable dosage forms include enteral (e.g., oral, intragastric, or transpyloric) dosage forms, parenteral (intramuscular, intravenous, intraperitoneal, rectal, vaginal, and subcutaneous) dosage forms, buccal dosage forms, and the like. Of course, as discussed below, dosing may need to be adjusted when folate is administered via a non-oral route, for example, to take into account very high instantaneous concentrations when the folate is administered intravenously, which can result in high percent urinary excretion.

Illustratively, the folate can be administered orally, such as in the form of an orally-administered supplement or an in the form of an orally-administered pharmaceutical composition. For example, pills, tablets, chewable tablets, capsules, powders, syrups, suspensions, solutions, chewable gums, liquid-filled candies, suckable candies, and soft chews are suitable forms for administration of the folate.

Sustained-release and enterically-protected formulations can also be used. By way of illustration, the folate can be administered orally in the form of a sustained-release folate formulation that includes folate incorporated in a matrix effective to release from about 4 to about 200 micromoles of the folate over a period of from about 4 hours to about 2 days (e.g., from about 4 hours to about 36 hours, from about 4 hours to about 24 hours, from about 4 hours to about 18 hours, from about 4 hours to about 12 hours, from about 4 hours to about 8 hours, etc.). By way of further illustration, the folate can be administered orally in the form of a sustained-release folate formulation that includes folate incorporated in a matrix effective to release the folate at a substantially constant rate of from about 0.4 micromole per hour to about 10 micromole per hour (e.g., from about 0.4 micromole per hour to about 8 micromole per hour, from about 0.4 micromole per hour to about 6 micromole per hour, from about 0.4 micromole per hour to about 4 micromole per hour, etc.). Methods for preparing such sustained-release formulations include those discussed hereinbelow.

Suitable dosage forms for orally administered reduced folate include tablets, dispersible powders, granules, capsules, suspensions, syrups, and elixirs. Inert diluents and carriers for tablets include, for example, lactose and talc. Tablets may also contain granulating and disintegrating agents, such as cellulose, starch, and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate. Other inert ingredients can also be present in the dosage forms for oral administration.

As discussed above, dosage forms for oral administration can include inert materials, such as fillers, binding agents, stabilizers, sweeteners, including nutritive sweeteners (e.g. sucrose, sorbitol, and other polyols) and non-nutritive sweeteners (e.g. saccharin, aspartame, and acesulfame K), colorants, flavors, buffers, salts, coatings, and the like that are known to those skilled in the art of supplement and pharmaceutical formulation.

Additionally or alternatively, the oral dosage forms or other compositions can also include one or more additional (i.e., in addition to the folate) biologically active materials.

Examples of such additional biologically active materials that can be present in the composition include: other vitamins (as well as precursors, derivatives, and isomers thereof) and/or nutrients (e.g., vitamin B1; vitamin B2; vitamin B3 (niacin); other vitamin B3 forms (e.g., niacinamide and inositol hexanicotinate); vitamin B5 (pantothenic acid); vitamin B6; vitamin B12 and its precursors and derivatives (e.g., cobalamin, cyanocobalamin, methylcobalamin, adenosylcobalamin, hydroxocobalamin, etc.); vitamin C; vitamin A and its precursors, such as beta-carotene; one or more of the various forms of vitamin D (e.g., vitamin D2, vitamin D3, etc.); vitamin E including vitamin E isomeric forms and derivatives; vitamin K; biotin; methionine; choline; taurine; carnitine; acetyl-carnitine; sugars; lipids; amino acids, such as glutamine, arginine, and methionine; and proteins), and minerals (e.g., boron, calcium, phosphorus, chromium, copper, manganese, magnesium, nickel, sodium, molybdenum, potassium, iron, selenium, silicon, vanadium, and zinc).

As further illustration, the additional biologically active materials which can be present in compositions that are useful in the methods of the present invention include essential nutrients, such as those that have been compiled in a number of published sources, including Modern Nutrition in Health and Disease, 8th ed., Shils et al., eds., Philadelphia:Lea and Febiger (1994); and Modern Nutrition in Health and Disease, 10th ed., Shils et al., eds., Philadelphia: Lippincott Williams & Wilkins (2005), which are hereby incorporated by reference.

The additional biologically active materials that can be present in the composition can be one that has been or may be associated with increased risk for NTD and/or other birth defects and/or disorders/pathologies of the mother or child. For example, women having deficiencies in certain nutrients (other than folate) have been found to be at increased risk of having NTD-affected pregnancies. Illustratively, several studies have examined B12 levels in either amniotic fluid, maternal serum, or cord blood in affected births compared to controls. Many, though not all, of these indicated significantly lower B12 in the cases relative to controls. One recent publication stratifying risk by B12 status in an Irish population recommended that women have a plasma B12 concentration of at least 300 pg/mL before becoming pregnant. A study of metallic micronutrients found significantly lower concentrations of zinc in maternal serum of NTD cases than in controls. Several lines of evidence in mice and case/control studies in humans have indicated a protective role for high choline intake. The "curly tail" mouse model has been found to have its high risk of NTD alleviated by administration of inositol, and a clinical trial in humans is currently underway. Serine hydroxymethyltransferase (SHMT1) knockouts in mice have been reported to increase the incidence of NTD, which is folate responsive. This has been suggested to also be responsible for some human NTD cases. Since SHMT is one of the routes for production of 5,10-methylene-THF, which in turn is responsible for biosynthesis of thymidylate nucleotide, it has been proposed that supplementation with nucleotides may be useful in preventing NTD.

As an alternative to administering the aforementioned additional biologically active materials (e.g., other vitamins, nutrients, minerals, and/or essential nutrients) as part of a composition which includes the folate, one or more of the additional biologically active material(s) can be administered separately from the folate, for example, in a separate dosage form (as in the case where the folate is administered orally in a first tablet and an additional biologically active material (e.g., vitamin B12, inositol, choline, etc.) is administered orally in a second tablet); by a different route (e.g., as in the case where the folate is administered orally and an additional biologically active material is administered non-orally or as in the case where the folate is administered non-orally and an additional biologically active material is administered orally); etc. For example, the folate can be administered orally and vitamin B12 can be administered intramuscularly. As yet another example, the folate can be administered orally in a first dosage form (e.g., a tablet or capsule), and inositol can be administered in a second dosage form (e.g., a second tablet, or multiple tablets, or as an oral solution or suspension). Where one or more of the additional biologically active material(s) are administered separately from the folate, the administration can be carried out at the same time, at substantially the same time, or at different times. Where the additional biologically active material(s) are administered separately from the folate, the additional biologically active material(s) and the folate can be packaged separately, or, alternatively, they can be packaged as part of kit, for example, as part of a kit that includes a pregnancy test device and the folate (e.g., as discussed further hereinbelow).

As will be apparent from the above discussion, compositions that are useful in the methods of the present invention can include one or more of the aforementioned additional (i.e., in addition to the folate) components, or, such compositions can be free or substantially free from one or more of the aforementioned additional components. By way of illustration, compositions that are useful in the methods of the present invention include those which are free or substantially free of additional biologically active materials. By way of illustration, compositions that are useful in the methods of the present invention include those which are free or substantially free of additional essential nutrients.

The folate can also be administered orally as a food that is fortified with one or more folates. Foods can be single-component foods, for example, fruits and fruit juices (e.g., orange juice), dairy products (e.g., milk), vegetables (e.g., spinach), other such single-component foods. Foods can also be multi-component preparations made from two or more single-component foods. Typically, foods contain various concentrations of endogenous reduced folates. Depending on the nature of the processing needed, the fortification is often optimally performed after any especially destructive processing steps, as is well know in the art of food fortification. Since the amount endogenous reduced folates present in the food can vary, it can be advantageous to know the final amount (number of moles) of reduced folate in the food or food preparation, as quantified, for example, by analysis of a sample of a product batch. Many analytical methods (such as microbial growth dependence, folate binding protein based assays, HPLC and GC) are available for measurement of the reduced folate content of foods, food preparations, and supplements.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intramuscular, intravenous, rectal, and subcutaneous administration. By way of illustration, the folate can be administered in a controlled release injectable formulation, such as the Medisorb Technology developed by Alkermers, Inc. described, for example, in U.S. Pat. Nos. 5,650,173, 5,654,008, and 5,656,297, which are hereby incorporated by reference.

Further details regarding formulating the compositions described hereinabove, such as compositions for enteral and parenteral administration, can be found, for example, in *Handbook of Pharmaceutical Excipients*, 3rd Edition (2000), American Pharmaceutical Association; *The Theory and Practice of Industrial Pharmacy*, 3rd Edition, Lachman et al. 1986; Pharmaceutical Dosage Forms: Tablets Volume Edition, Christopher T, edition, 1995; and Remington's Pharmaceutical Sciences, 2000, which are hereby incorporated by reference.

The natural 6-position isomers of tetrahydrofolic acid or one-carbon derivatives are preferred, such as (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives thereof. The natural 6S-chirality (l-form) of the glutamate, or glutamates is also preferred.

The tetrahydrofolic acid or one-carbon derivatives can also be mixtures, including the racemic mixture, of the natural 6-position isomer and the unnatural 6-position isomer. The unnatural 6-position isomers do not participate in any known biochemical reaction, and, thus, when a dose is specified, this is to be understood in terms of the content of the natural isomer. The unnatural isomers, however, can bind to and be transported by some folate transporters. Thus, they can inhibit the uptake of the active natural isomers. No toxicity has yet to be ascribed to the unnatural tetrahydrofolic acid or one-carbon derivatives, but their pharmacokinetics in animals and humans can be different from that of the natural isomers. Thus, although mixtures of the 6-position isomers can be used (such as the racemic mixture), it is preferred that the natural isomer content be greater than 90% (e.g., greater than 95%, greater than 97%, etc.).

As mentioned above, the folate can also be a mixture of folic acid and/or one or more of the above-mentioned tetrahydrofolic acid or one-carbon derivatives (e.g., a mixture of 5-methyl-(6S)-tetrahydrofolic acid and 5-formyl- (6S)-tetrahydrofolic acid; a mixture of 5-methyl-(6S)-tetrahydrofolic acid and folic acid; etc.). When a dose is set forth herein, this dose is given in terms of the total micromoles of folic acid and all of the natural 6-position isomers of reduced folates present. It is also noted that, at the doses indicated herein, a large fraction of orally-administered tetrahydrofolic acid or one-carbon derivative will be rapidly converted to 5-methyltetrahydrofolate upon uptake from the gastrointestinal tract.

Despite a great deal of experience administering tetrahydrofolic acid or one-carbon derivatives in the dose ranges described herein to both animals and humans, with the exception of a rare allergic reaction, few adverse effects have been reported. Most of this experience has been with 5-formyl-tetrahydrofolate (both as the racemic mixture (leucovorin) and as the natural isomer) and 5-methyl-tetrahydrofolate (both as the racemic mixture and as the natural isomer). Nausea has been reported in some cases with use of leucovorin, but this may be due to the effects of coadministered drugs, such as fluorouracil for the treatment of various cancers. Seizures have been reported in people prone to epilepsy when given doses higher than those described herein. Nonetheless, precaution should be exercised with epileptic patients. It has been admonished that leucovorin, like folic acid, should not be administered to a person who is deficient in vitamin B12 as this can mask macrocytic anemia and possibly also exacerbate degeneration of the central nervous system. This potential effect can be counteracted by the simultaneous administration of vitamin B12, which has the added benefit of also decreasing the risk of neural tube defect. Masking of macrocytic anemia by 5-methyl-tetrahydrofolate has not been reported, and may not even be operative due to the methyl trap concept of B12 deficiency. For this reason (among others), 5-methyl-tetrahydrofolic acid may have advantages over tetrahydrofolic acid and other one carbon derivatives, such as 5-formyl-tetrahydrofolic acid, as well as over folic acid.

Recently, concern has been raised over potential detrimental effects of folic acid, especially when administered to women of child bearing age. Increased incidence of asthma and lower respiratory tract infections in the off-spring have been reported. Animal models suggest potential increased risk for certain cancers. It is currently unknown whether these observations are related specifically to folic acid or more generally to any folate intake. It has been speculated that unmetabolized folic acid arising from the incomplete conversion of folic acid in humans may be responsible for some of these findings, though this has not been established. The rapid repletion protocol described herein may help minimize overall exposure to folate since the folate is only given in high dose for a relatively short period (during the repletion phase). The optional maintenance phase provides folate at a level that a woman or pregnant women would be administered as a result of current practice.

As mentioned above, in certain aspects of the present invention, the repletion doses include no less than about 2.5 micromole of folate. Suitable repletion doses include no less than about 3 micromole of folate, no less than about 4 micromole of folate, no less than about 5 micromole of folate, no less than about 6 micromole of folate, no less than about 7 micromole of folate, no less than about 8 micromole of folate, no less than about 9 micromole of folate, greater than 9 micromole of folate, no less than 9.1 micromole of folate, greater than 9.1 micromole of folate, no less than 9.2 micromole of folate, no less than 10 micromole of folate, no less than 10.5 micromole of folate, greater than 10.9 micromole of folate, no less than about 10.9 micromole of folate, greater than 11 micromole of folate, greater than 11.3 micromole of folate, no less than 11.4 micromole of folate, greater than 11.4 micromole of folate, greater than 11.5 micromole of folate, no less than 11.5 micromole of folate, no less than about 11.5 micromole of folate, from about 2.5 micromole to about X micromole of folate, from about 3 micromole to about X micromole of folate, from about 4 micromole to about X micromole of folate, from about 5 micromole to about X micromole of folate, from about 6 micromole to about X micromole of folate, from about 7 micromole to about X micromole of folate, from about 8 micromole to about X micromole of folate, from about 9 micromole to about X micromole of folate, from greater than 9 micromole to about X micromole of folate, from 9.1 micromole to about X micromole of folate, from greater than 9.1 micromole to about X micromole of folate, from 9.2 micromole to about X micromole of folate, from 10 micromole to about X micromole of folate, from 10.5 micromole to about X micromole of folate, from 10.9 micromole to about X micromole of folate, from about 10.9 micromole to about X micromole of folate, from greater than 11 micromole to about X micromole of folate, from greater than 11.3 micromole to about X micromole of folate, from 11.4 micromole to about X micromole of folate, from greater than 11.4 micromole to about X micromole of folate, from greater than 11.5 micromole to about X micromole of folate, from 11.5 micromole to about X micromole of folate, and/or from about 11.5 micromole to about X micromole of folate, wherein X is independently selected from 35, 50, 100, and 200.

The repletion doses (e.g., the doses which include no less than about 2.5 micromole of folate) can, for example, be administered no less than about 4 hours apart and no more than about one day apart. By way of example, the doses can be administered at 3-hour intervals, at 4-hour intervals, at 6-hour intervals, at 8-hour intervals, at 12-hour intervals, at 18-hour intervals, at 24-hour intervals, etc.

It will be appreciated that the dosing intervals mentioned here and elsewhere in the application, while ideally uniform, can be tailored to suit the individual's schedule. Thus, for example, where the present application refers to a Z-hour interval (e.g., 4-hour interval) or to doses being administered Z hours apart (e.g., 4 hours apart), it shall be understood that this refers to 24/Z doses per day (e.g., 24/4=6) doses per day which are spaced substantially uniformly apart (e.g., as uniformly apart as is practical for the women). By way of illustration, where the present application calls for a 6-hour interval or to doses being administered 6 hours apart, it shall be understood that administration of such doses at 8:15 am, 1:00 pm, 6:00 pm, and 10:30 pm would satisfy such a requirement.

It will also be appreciated that the intervals and/or doses, while they can be and typically are substantially uniform, need not be so, for example, as in those cases where the doses vary but the intervals do not (e.g., a first dose of 20 micromole, a second dose of 12 micromole administered 12 hours after the first dose, and third dose of 6 micromole administered 12 hours after the second dose); as in those cases where the intervals vary but the doses do not (e.g., a first dose of 20 micromole, a second dose of 20 micromole administered 12 hours after the first dose, and third dose of 20 micromole administered 6 hours after the second dose); and as in those cases where both the doses and the intervals vary (e.g., a first dose of 20 micromole, a second dose of 12 micromole administered 12 hours after the first dose, and third dose of 8 micromole administered 6 hours after the second dose).

As mentioned above, in certain aspects of the present invention, the method includes administering two or more repletion doses of folate, provided that the total number of repletion doses administered to the woman is 72 or fewer. For example, the method can include the administration of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 repletion doses. By way of illustration, methods of the present invention can further include administering to the woman a third repletion dose of folate, wherein the third repletion dose comprises no less than about 2.5 micromole of folate and wherein the third repletion dose is administered no more than about one day after the second repletion dose is administered. Examples of suitable doses for the third repletion dose include those mentioned above in connection with the first two repletion doses.

The repletion doses are generally administered for a limited period of time. For example, the repletion doses can be administered to the woman for no more than 12 days, for no more than 11 days, for no more than 10 days, for no more than 9 days, for no more than 8 days, for no more than 7 days, for no more than 6 days, for no more than 5 days, for no more than 4 days, for no more than 3 days, for no more than 2 days, for no more than 36 hours, for no more than 1 day, for between 2 days and 12 days, for between 36 hours and 7 days, etc.

As one skilled in the art will appreciate, selection of the dose, dosing interval, total number of doses, and total time over which the repletion doses are administered can be interrelated and can depend on other factors as well.

For example, in certain embodiments, when the two or more repletion doses of folate are administered about one day apart, at least one of the two or more repletion doses can include greater than 11.5 micromole of folate (e.g., as in cases where each of the two or more repletion doses includes greater than 11.5 micromole of folate).

By way of further illustration, in certain embodiments, the dose and dosing interval are selected such that the total amount of folate administered to the woman per day is greater than 11.5 micromole.

As mentioned above, in certain aspects of the present invention, the method includes administering folate to the woman during a repletion phase, wherein the total amount of folate administered to the woman per day during the repletion phase is greater than about 10 micromole and no greater than about 200 micromole, e.g., from about 11.5 micromole to about 200 micromole, greater than about 11 micromole and no greater than about X micromole, greater than about 12 micromole and no greater than about X micromole, greater than about 13 micromole and no greater than about X micromole, greater than about 14 micromole and no greater than about X micromole, greater than about 15 micromole and no greater than about X micromole, greater than about 16 micromole and no greater than about X micromole, greater than about 17 micromole and no greater than about X micromole, greater than about 18 micromole and no greater than about X micromole, greater than about 19 micromole and no greater than about X micromole, greater than about 20 micromole and no greater than about X micromole, greater than about 22 micromole and no greater than about X micromole, greater than about 24 micromole and no greater than about X micromole, greater than about 26 micromole and no greater than about X micromole, greater than about 28 micromole and no greater than about X micromole, greater than about 30 micromole and no greater than about X micromole, greater than about 35 micromole and no greater than about X micromole, greater than about 40 micromole and no greater than about X micromole, greater than about 45 micromole and no greater than about X micromole, greater than about 50 micromole and no greater than about X micromole, greater than about 55 micromole and no greater than about X micromole, etc., wherein X is independently selected from, e.g., 50, 75, 100, 150, and 200.

Illustratively, in certain embodiments, during the repletion phase, folate is administered to the woman once per day in a single dose. In other embodiments, folate is administered to the woman multiple times per day in discrete doses, such as in the case where folate is administered to the woman multiple times per day in discrete doses for two or more days. Continuous administration can also be used, as in the case where, during the repletion phase, folate is administered to the woman in a sustained-release dosage form, for example as discussed hereinabove.

As yet further illustration, in certain embodiments, the dose and number of doses are selected such that the cumulative amount of folate contained in the repletion doses administered to the woman (i.e., the total amount of folate administered to the woman over the entire course of the repletion phase) is from about 30 micromole to about 500 micromole, such as from about 30 micromole to about 400 micromole, from about 30 micromole to about 300 micromole, from about 30 micromole to about X micromole, where X is 250, 200, 150, 120, 110, 100, etc. As still further illustration, in certain embodiments, the dose and number of doses are selected such that the cumulative amount of folate contained in the repletion doses administered to the woman is from about 30 micromole to about 150 micromole (e.g., 30±2.5, 35±2.5, 40±2.5, 45±2.5, 50±2.5, 55±2.5, 60±2.5, 65±2.5, 70±2.5 75±2.5, 80±2.5, 85±2.5, 90±2.5, 95±2.5, 100±2.5, 105±2.5, 110±2.5, 115±2.5, 120±2.5, 125±2.5, 130±2.5, 135±2.5, 140±2.5, 145±2.5, 150±2.5 micromoles).

Illustratively, if 5-methyl-6S-THF is used, individual doses can contain between about 2.7 mg to 16 mg based on the content of free acid. Intervals of 6, 8, 12, and 24 hours can be used. This first phase of treatment (i.e., the phase during which repletion doses are administered, also referred to herein as the "repletion phase") can be continued until the cumulative total amount of folate (e.g., the cumulative total amount of folic acid plus all natural isomers of tetrahydrofolic acid or one-carbon derivatives thereof) reaches between about 30 to about X micromoles (where X is, e.g., 500, 400, 300, 250, 200, 150, 120, 100, etc.). For example, a woman can be administered 16.3 micromole of folate (e.g., 7.5 mg of 5-(6S)-methyl-6S-THF or 15 mg of racemic 5-methyl-6S-THF, both of which contain 16.3 micromole of 5-(6S)-methyl-6S-THF) three or four times at intervals of 24 hours to give a total cumulative amount of 49 or 65.2 micromole of folate, respectively. Using this 24 hour schedule, most women would achieve sufficiently protective folate levels by between 48 hours and 72 hours, respectively, and could initiate a second phase of treatment (during which lower, maintenance doses of folate are administered, also referred to herein as the "maintenance phase" (discussed further hereinbelow)) by 72 hours and 96 hours, respectively. Alternatively, the same three or four repletion doses can be administered every 12 hours, and the maintenance phase initiated after 36 or 48 hours, respectively. As another example, a woman can be administered 5.5 mg of 5-methyl-6S-THF (12 micromoles of folate) three times a day for three days to give total cumulative folate amount of 108 micromoles. Generally, this first phase (i.e., repletion phase) of should last for no more than 12 days (e.g., no more than 7 days, no more than 4 days, no more than 3 days, no more than 2 days, no more than 1 day, etc.). A woman who is heavier than average or who has very low folate levels before treatment may benefit from a higher dose level or from extension of first phase (i.e., repletion phase) of treatment. For a subject known or suspected to be epileptic, it may be advisable to use a somewhat lower dose of folic acid and/or of reduced folate) and to either extend to the duration of the repletion phase or to consume the lower dose more frequently (e.g., at a frequency greater than once per day).

As further illustration, a woman can be administered 16.3 micromole of folate (e.g., 7.5 mg of 5-(6S)-methyl-6S-THF or 15 mg of racemic 5-methyl-6S-THF, both of which contain 16.3 micromole of 5-(6S)-methyl-6S-THF) five times at intervals of 12 hours to give a total cumulative amount of 81.7 micromole of folate in 60 hours. Alternatively, a woman can be administered 21.7 micromole of folate (e.g., 10 mg of 5-(6S)-methyl-6S-THF or 20 mg of racemic 5-methyl-6S-THF, both of which contain 21.7 micromole of 5-(6S)-methyl-6S-THF) five times at intervals of 12 hours to give a total cumulative amount of 108.5 micromole of folate in 60 hours.

Continuous administration of the folate (e.g., in a sustained-release formulation) can be convenient in many cases. For example, a sustained-release dosage form having 32.7 micromole of folate (15 mg in the case of 5-methyl-6S-THF) in a formulation designed to release the folate over 24 hours would be simpler than consuming two doses of 16.3 micromoles each day and, thus, may produce higher compliance. This could also lead to more uniform plasma folate levels throughout the day by decreasing the peak (Cmax) level and, at the same time, increasing the minimum level. Such a sustained-release formulation can also be useful for those susceptible to epilepsy.

As a further example, 81.7 micromoles (e.g. 37.5 mg of 6S-5-MTHF) can be contained in a sustained release formulation designed to release over 2 days.

As discussed above, the folate (e.g., folic acid and/or tetrahydrofolic acid or one-carbon derivative) administered in the first (i.e., repletion) phase can include additional nutrients. For example, it can include vitamin B12 (e.g., as the hydroxo, cyano, methyl, adenosyl, or glutathionyl form or as a combination of such forms). The amount of vitamin B12 per dose of tetrahydrofolate or one-carbon derivative can range from about 0.25 mg to about 10 mg (e.g., about 0.25 mg, about 0.5 mg, about 1 mg, about 2 mg, about 3 mg, about 5 mg, about 10 mg, between about 0.5 and about 3 mg, etc.). As a further example, a repletion dose of 7.5 mg dose of 5-methyl-6S-THF can also include 0.5, 1.0, or 2.0 mg of cyanocobalamin or methylcobalamin. These additional nutrients can be administered separately (e.g., in a separate tablet or capsule) or in combination with the folate (e.g., in a single tablet or capsule containing both the folate and the additional nutrient(s). In the case of vitamin B12, when administered separately, the vitamin B12 can be administered orally, sublingually, intranasally, or by injection (such as intramuscular). For example, when administered separately and orally, suitable vitamin B12 daily doses can range from about 0.25 mg to about 10 mg (e.g., about 0.25 mg, about 0.5 mg, about 1 mg, about 2 mg, about 3 mg, about 5 mg, about 10 mg, between about 0.5 and about 3 mg, etc.). The duration of B12 administration can be the same as or longer than the folate repletion phase.

In those cases where vitamin B12 is administered with the folate (either separately or together), it may be advantageous to also administer a N-[8-(2-hydroxybenzoyl)amino]caprylate salt (e.g., sodium N-[8-(2-hydroxybenzoyflamino] caprylate) or other such penetration enhancer, for example, as described in Castelli et al., "Pharmacokinetics of Oral Cyanocobalamin Formulated With Sodium N-[8-(2-hydroxybenzoyl)amino]caprylate (SNAC): An Open-Label, Randomized, Single-Dose, Parallel-Group Study in Healthy Male Subjects," *Clinical Therapeutics*, 33(7):934-945 (2000) ("Castelli I"); U.S. Patent Application Publication No. 2011/0207693 of Castelli ("Castelli II"); and Ross et al., "Gastrointestinal Absorption of Heparin by Lipidization or Coadministration with Penetration Enhancers," *Current Drug Delivery*, 2:277-287 (2005) ("Ross"), which are hereby incorporated by reference.

As discussed above, the folate can be folic acid or tetrahydrofolic acid or a one-carbon derivative thereof or combinations thereof. In certain embodiments, the folate administered is a combination of folic acid and one or more reduced folates (e.g., tetrahydrofolic acid or a one-carbon derivative thereof, such as 5-methyl-6S-THF), for example, as in the case where the folate is administered twice per day as a mixture of 400 µg of folic acid and 7.5 mg of 5-methyl-6S-THF and as in the case where the folate is administered twice per day as a mixture of 200 µg of folic acid and 7.5 mg of 5-methyl-6S-THF. In certain embodiments, the predominant folate administered is one or more reduced folate (e.g., tetrahydrofolic acid or a one-carbon derivative thereof, such as 5-methyl-6S-THF). In certain embodiments, the folate administered is one or more reduced folates (e.g., tetrahydrofolic acid or a one-carbon derivative thereof, e.g., 5-methyl-6S-THF), and no folic acid is administered.

As mentioned above, the method of the present invention can also include, subsequent to administration of the repletion doses, administering to the woman maintenance doses of folate at a daily dosage of greater than about 0.4 micromole and less than the daily repletion dose. As discussed hereinabove, the repletion doses generally are, but need not be, the same. In those cases where the daily repletion doses are not all the same, "less than the daily repletion dose" means "less than the lowest daily repletion dose". Illustrative daily maintenance doses of folate include about 0.4 micromole, about 0.5 micromole, from about 0.4 micromole to about 0.5 micromole, about 0.9 micromole, about 1 micromole, from about 0.9 micromole to about 1 micromole, about 4.5 micromole, about 9 micromole, from about 4 micromole to about 9.5 micromole, greater than about 0.4 micromole and less than 10 micromole, greater than about 0.9 micromole and less than 10 micromole, greater than about 0.4 micromole and less than about 5 micromole, greater than about 0.9 micromole and less than about 5 micromole, and the like). It will be appreciated that higher daily maintenance doses of folate can be used, provided that the daily maintenance dose is selected so as to be less than the daily repletion dose. For example, where a daily repletion dose of 15 micromole is used, suitable daily maintenance doses of folate include about 10 micromole, about 11 micromole, 11.3 micromole, 12 micromole, and the like. The maintenance doses can be administered by any of the routes discussed above for administration of the repletion doses. The aforementioned daily maintenance dose can be administered as a single dose (e.g., in a single tablet or capsule taken once per day), or it can be administered in multiple doses (e.g., 2, 3, 4, etc.) taken at regular intervals throughout the day. It will be appreciated that, while the daily maintenance doses generally are the same, they need not be so. For example, a daily maintenance dose of 2.7 micromole can be administered for the first four days of the maintenance phase, and then a daily maintenance dose of 1.8 micromole can be administered for the remainder of the maintenance phase. The maintenance doses can include one or more of the other vitamins and/or nutrients (e.g., vitamin B1, vitamin B12, etc.) discussed above in connection with the discussion of the repletion doses. In certain embodiments, the maintenance doses are administered about once per day and each maintenance dose includes less than 2.5 micromole of folate.

For example, following the first phase (repletion phase) of the rapid repletion method of the present invention, the higher folate levels (and higher B12 status, in cases where the repletion phase also included administering vitamin B12) that is achieved can be maintained by administration of a folate dose containing a lower amount of folic acid or tetrahydrofolic acid or a one-carbon derivative thereof (e.g., 5-methyl-6S-THF) or combinations thereof. The folate administered during the maintenance phase can be in the form of a multivitamin. The daily dose of folate in this maintenance phase can be the value specified by the Institute of Medicine as the Recommended Dietary Allowance for pregnant (currently 600 µg/d Dietary Folate Equivalents ("DFE")) or lactating women (currently 500 µg/d DFE), or the Daily Value established by the FDA (currently 800 µg/d), or an amount thought appropriate by a manufacturer of prenatal vitamin product, or an amount thought appropriate by or other national regulatory agencies. The typical total folate content of prenatal vitamins ranges from 0.4 to 1.0 mg per day, although some are as high as 4 or 5 mg per day (for women who have previously had an NTD birth. This phase could also be maintained by a typical over-the-counter multivitamin or single entity folate product, although a product designed for prenatal support may be preferred in certain situations. This maintenance phase can be continued for several months, for the remainder of the pregnancy, or even after delivery while the woman is lactating.

As mentioned above, in certain embodiments, during the repletion phase, folate is administered to the woman multiple times per day in discrete doses. In such cases, it may be convenient to have one (or more) of these repletion doses contain an amount of folate equal to the amount of folate that is to be administered during the maintenance phase. For example, during the repletion phase, two 5-mg doses of folate and one 0.6 mg dose of folate can be administered to the woman per day, followed by a maintenance phase during which one 0.6 mg dose of folate is administered to the woman per day. By way of further illustration, the repletion phase can consist of administration of two 5-mg doses per day along with a typical over-the-counter or prescription multivitamin or single entity folate product, preferably having a prenatal formulation (as discussed above in the previous paragraph); and, following this, during the maintenance phase, administration of the typical over-the-counter or prescription multivitamin or single entity folate product (e.g., the one having a prenatal formulation) would continue, while administration of the two 5-mg doses would be discontinued.

As discussed below, it has been unexpectedly discovered that the elevated plasma folate levels achieved during the first phase (i.e., the repletion phase) of the method of the present invention can be maintained with a lower dose close to the Daily Value.

As discussed in greater detail hereinbelow in Example 4, neural tube closure is believed to be complete by about 28 days after conception; cardiac neural crest cells are believed to enter the aortic arches and nascent outflow tracts between 32 to 37 days after conception; cardiac outflow tract and ventricular septation are believed to be complete by about 8 weeks after conception; lip closure is believed to occur by 35 to 40 days after conception; palate closure is believed to occur by 7 to 10 weeks after conception. Accordingly, while benefits of the rapid repletion methods of the present invention can be attained by initiating rapid repletion at any stage of pregnancy (e.g., to promote higher birthweights), such as during the first two trimesters of pregnancy, during the first trimester of pregnancy, etc., certain benefits can only be attained by initiating the first phase (repletion stage) early in pregnancy.

For example, in order to maximize the benefits of the present invention (especially with respect to reducing the risk of having an NTD affected birth), it is preferred that the repletion phase be started and completed as soon as possible after conception. Thus, it will be appreciated that selection of the dose, dosing interval, total number of doses, and total time over which the repletion doses can depend on when the woman conceived and when the woman (or her physician, etc.) first becomes aware that she may be pregnant.

In certain embodiments, the first repletion dose of folate is administered within 39 days (e.g., within 36 days, within 34 days, within 32 days, within 30 days, within 28 days, within 27 days, within 26 days, within 25 days, within 24 days, within 23 days, within 22 days, within 21 days, within 20 days, within 19 days, within 18 days, within 17 days, within 16 days, within 15 days, within 14 days, within 13 days, within 12 days, within 11 days, within 10 days, etc.) after conception. In certain embodiments, the first repletion dose of folate is administered within 11 days (e.g., within 10 days, within 9 days, within 8 days, within 7 days, within 6 days, within 5 days, within 4 days, within 3 days, within 2 days, within 1 day, etc.) of a missed menses. In certain embodiments, the first repletion dose of folate is administered within 13 days (e.g., within 12 days, within 11 days, within 10 days, within 9 days, within 8 days, within 7 days, within 6 day, within 5 days, within 4 days, within 3 days, within 2 days, within 1 day, etc.) of a positive pregnancy test (e.g., a positive hCG pregnancy test) or any other indication of pregnancy.

In certain embodiments, the final repletion dose of folate is administered within 40 days (e.g., within 37 days, within 35 days, within 33 days, within 31 days, within 29 days, within 28 days, within 27 days, within 26 days, within 25 days, within 24 days, within 23 days, within 22 days, within 21 days, within 20 days, within 19 days, within 18 days, within 17 days, within 16 days, within 15 days, within 14 days, within 13 days, within 12 days, within 11 days, within 10 days, etc.) after conception. In certain embodiments, the final repletion dose of folate is administered within 13 days (e.g., within 12 days, within 11 days, within 10 days, within 9 days, within 8 days, within 7 days, within 6 days, within 5 days, within 4 days, within 3 days, within 2 days, within 1 day, etc.) of a missed menses. In certain embodiments, the final repletion dose of folate is administered within 15 days (e.g., within 14 days, within 13 days, within 12 days, within 11 days, within 10 days, within 9 days, within 8 days, within 7 days, within within 5 days, within 4 days, within 3 days, within 2 days, within 1 day, etc.) of a positive pregnancy test (e.g., a positive hCG pregnancy test) or any other indication of pregnancy.

As mentioned above, in certain aspects of the present invention, the method includes administering folate to the woman during a repletion phase, wherein the amount of folate administered per dose and the number of doses administered per day are selected such that the woman's minimum plasma folate level does not fall below 35 nM (e.g., does not fall below 40 nM, does not fall below 45 nM, etc.) and wherein the repletion phase is carried out for no more than about 12 days (e.g., for no more than 8 days, for no more than 6 days, for no more than 4 days, etc.). Examples of suitable folates, doses, and dosing intervals, and times for commencing the repletion phase include those set forth hereinabove. By way of further illustration, the amount of folate administered per dose and the number of doses administered per day can be selected such that:

(1) when the dosing interval is every 3 hours (i.e., 8 doses per day), the amount of folate administered per dose is between about 1.1 micromole and 4.4 micromole (e.g., about 2.2 micromole);
(2) when the dosing interval is every 4 hours (i.e., 6 doses per day), the amount of folate administered per dose is between about 2 micromole and 8 micromole (e.g., about 4 micromole);
(3) when the dosing interval is every 6 hours (i.e., 4 doses per day), the amount of folate administered per dose is between about 3.9 micromole and 15.4 micromole (e.g., about 7.7 micromole);
(4) when the dosing interval is every 8 hours (i.e., 3 doses per day), the amount of folate administered per dose is between about 6 micromole and 23 micromole (e.g., about 11.5 micromole);
(5) when the dosing interval is every 12 hours (i.e., 2 doses per day), the amount of folate administered per dose is between about 8.2 micromole and 32.6 micromole (e.g., about 16.3 micromole); and
(6) when the dosing interval is every 24 hours (i.e., 1 dose per day), the amount of folate administered per dose is between about 18.5 micromole and 74 micromole (e.g., about 37 micromole).

As will be apparent from the above discussion, the methods of the present invention for rapidly repleting folate levels of a woman for whom there is reason to believe that she may be pregnant or of a woman who believes that she may soon become pregnant can useful, for example, to reduce the woman's risk of having a fetus with a neural tube defect, a heart defect, and/or an orofacial cleft defect. Accordingly, the present invention also relates to methods for reducing a woman's risk of having a fetus with a neural tube defect, a heart defect, and/or an orofacial cleft defect. One such method includes administering to the woman two or more repletion doses of folate, wherein each of the repletion doses comprises no less than about 2.5 micromole of folate, wherein the repletion doses are administered no more than about one day apart, and wherein the total number of repletion doses administered to the woman is 72 or fewer. Another such method includes administering folate to the woman during a repletion phase, wherein the total amount of folate administered to the woman per day during the repletion phase is greater than about 10 micromole and no greater than about 200 micromole and wherein the repletion phase is carried out for no more than about 12 days. Yet another such method includes administering folate to the woman during a repletion phase, wherein the amount of folate administered per dose and the number of doses administered per day are selected such that the woman's minimum plasma folate level does not fall below 35 nM and wherein the repletion phase is carried out for no more than about 12 days. Still other such methods include administering to the woman two or more repletion doses comprising reduced folate and, optionally, folic acid, wherein each of the repletion doses comprises no less than about 2.5 micromole of reduced folate and optional folic acid and wherein the repletion doses are administered no more than about one day apart. Yet other such methods include administering reduced folate and, optionally, folic acid to the woman during a repletion phase, wherein the total amount of reduced folate and optional folic acid administered to the woman per day during the repletion phase is greater than about 10 micromole and no greater than about 200 micromole.

Suitable folates for use in these methods include those discussed above. For example, the folate can be a reduced folate (e.g., 5-methyl-THF, alone or in combination with other reduced folates); or it can be a combination of one or more reduced folates and folic acid; or it can be folic acid (unless for those methods which explicitly call for the use of a reduced folate and, optionally, folic acid). In certain embodiments, at least a portion of the folate used is a reduced folate, for example, (1) as in the case where the mole fraction of reduced folate to total folate (i.e., RF/(RF+FA), where RF is the moles of reduced folate and FA is the moles of folic acid) is at least about 0.1 (e.g., at least about 0.2, at least about 0.3, at least about 0.4, at least about 0.5, at least about 0.6, at least about 0.7, at least about 0.8, at least about 0.9, 0.95, 0.98, etc.) and (2) as in the case where the total folate includes about 0.9 millimole (e.g., about 0.4 mg) of folic acid with the remainder being reduced folate (e.g., 5-methyl-THF or a mixture of 5-methyl-THF and other reduced folates). Without intending to be bound by theory, applicants believe that the use of reduced folates may be more effective than the use of folic acid in reducing the woman's risk of having a fetus with a neural tube defect, a heart defect, and/or an orofacial cleft defect.

As mentioned above, the methods of the present invention can be carried out with a sustained-release formulation, such as the sustained release formulations described below, to which the present also relates.

The present invention, in yet another aspect thereof, relates to a sustained-release formulation that is suitable for administration to a woman for whom there is reason to believe that she may be pregnant or of a woman who believes that she may soon become pregnant. The sustained-release formulation includes a reduced folate and, optionally, folic acid incorporated in a matrix effective to release from about 4 to about 200 micromoles (e.g., from greater than 5 to about 200 micromoles, from 5.5 to about 200 micromoles, from about 5.5 to about 200 micromoles, from 6 to about 200 micromoles, from about 6 to about 200 micromoles, from 6.5 to about 200 micromoles, from about 6.5 to about 200 micromoles, from about 7 to about 200 micromoles, from greater than 8 to about 200 micromoles, from 8.5 to about 200 micromoles, from about 8.5 to about 200 micromoles, from 9 to about 200 micromoles, from about 9 to about 200 micromoles, from 9.5 to about 200 micromoles, from about 9.5 to about 200 micromoles, from about 10 to about 200 micromoles, from about 11 to about 200 micromoles, from about 11.5 to about 200 micromoles, from about 12 to about 200 micromoles, from about 20 to about 200 micromoles, etc.) of the reduced folate and optional folic acid over a period of from about 4 hours to about 2 days (e.g., from about 4 hours to about 36 hours, from about 4 hours to about 24 hours, from about 4 hours to about 18 hours, from about 4 hours to about 12 hours, from about 4 hours to about 8 hours, etc.).

For example, the sustained-release formulation can include a reduced folate and, optionally, folic acid incorporated in a matrix effective to release from about 4 to about 100 micromole (e.g., from about 10 to about 100 micromoles, from about 11 to about 100 micromoles, from about 11.5 to about 100 micromoles, from about 12 to about 100 micromoles, from about 20 to about 100 micromoles, etc.), or from about 4 to about 50 micromole (e.g., from about 10 to about 50 micromoles, from about 11 to about 50 micromoles, from about 11.5 to about 50 micromoles, from about 12 to about 50 micromoles, from about 20 to about 50 micromoles, etc.) of the reduced folate and optional folic acid over a period of from about 4 hours to about 2 days (e.g., from about 4 hours to about 36 hours, from about 4 hours to about 24 hours, from about 4 hours to about 18 hours, from about 4 hours to about 12 hours, from about 4 hours to about 8 hours, etc.). By way of further illustration, the sustained-release formulation can include a reduced folate and, optionally, folic acid incorporated in a matrix effective to release from about 4 to about 50 micromoles (e.g., from about 4 to about 20 micromoles) over a period of from about 4 to about 12 hours (e.g., from about 4 to about 8 hours); from about 11 to about 50 micromoles (e.g., from about 11.5 to about 50 micromoles, from about 12 to about 50 micromoles, from about 20 to about 50 micromoles, etc.) over a period of from about 8 to about 24 hours (e.g., from about 12 to about 24 hours); etc.

The amount of reduced folate and optional folic acid contained in a particular sustained-release formulation can depend on a variety of factors, including the intended frequency of administration and the period over which the reduced folate and optional folic acid are released. For example, the sustained-release formulation can be formulated and administered so as to provide daily dosages of folate (i.e., reduced folate and optional folic acid) in the ranges described hereinabove in the context of the total amount of folate administered to the woman per day during the repletion phase the present invention's methods. Illustratively, the sustained-release formulation can be formulated and administered so as to provide daily dosages of from about 10 micromole to about 200 micromole of folate (i.e., reduced folate and optional folic acid). By way of illustration, a sustained-release formulation, formulated so as to release 40 micromoles of reduced folate and optional folic acid over an 8 hour period and administered 3 times per day, would provide a daily dosage of 120 micromoles of reduced folate and optional folic acid. Expressed differently, such a sustained-release formulation is formulated so as to release 5 micromoles of reduced folate and optional folic acid per hour on average.

In certain embodiments, the sustained-release formulation is formulated so as to release, on average, between about 0.4 micromoles and about 8.5 micromoles of reduced folate and optional folic acid per hour.

Suitable reduced folates for use in the sustained-release formulations include those described hereinabove. For example, the reduced folate can be selected from the group consisting of tetrahydrofolic acid, 5-methyl-tetrahydrofolic acid, 5-formyl-tetrahydrofolic acid, 10-formyl-tetrahydrofolic acid, 5,10-methylene-tetrahydrofolic acid, 5,10-methenyl-tetrahydrofolic acid, 5-formimino-tetrahydrofolic acid, 7,8-dihydrofolic acid, and polyglutamyl derivatives thereof. Illustratively, in certain embodiments, the reduced folate is 5-methyl-tetrahydrofolic acid or a polyglutamyl derivative thereof. By way of further illustration, in certain embodiments, the reduced folate is substantially chirally pure (e.g., greater than 90% chiral purity) 5-methyl-(6S)-tetrahydrofolic acid or a polyglutamyl derivative thereof; while in other embodiments, the reduced folate is racemic 5-methyl-(6)-tetrahydrofolic acid or a polyglutamyl derivative thereof.

In certain embodiments, the sustained-release formulation does not include the optional folic acid. In such cases, the amount of reduced folate and optional folic acid released from the sustained-release formulation refers to the amount of reduced folate released from said formulation.

In certain embodiments, the sustained-release formulation further includes the optional folic acid. In such cases, the amount of reduced folate and optional folic acid released from the sustained-release formulation refers to the sum of (1) the amount of reduced folate released from said formulation and (2) the amount of folic acid released from said formulation.

The sustained-release formulation can further include other biologically active materials, such as those described hereinabove. For example, the sustained-release formulation can further include vitamin B12. In certain embodiments, the sustained-release formulation further includes vitamin B12 in an amount that is greater than about 400% (e.g., greater than about 500%, greater than about 600%, greater than about 700%, greater than about 800%, greater than about 1000%, greater than about 1500%, greater than about 2000% of the recommended daily allowance of vitamin B12. As used herein, "recommended daily allowance of Vitamin B12" is meant to refer to the recommended daily allowance of vitamin B12 in the United States, which is 6 μg/day. Illustratively, the sustained-release formulation can further include vitamin B12 in an amount greater than about 30 microgram (e.g., greater than about 40 microgram, greater than about 50 microgram, greater than about 60 microgram, greater than about 0.1 mg, greater than about 0.25 mg, greater than about 0.5 mg, greater than about 1 mg, greater than about 2 mg, greater than about 3 mg, greater than about 5 mg, greater than about 10 mg, etc.).

In those cases where sustained-release formulation includes vitamin B12, the formulation can also include sodium N-[8-(2-hydroxybenzoyl)amino]caprylate or other such penetration enhancers, for example, as discussed hereinabove in the context of the method claims of the present invention and as described further in Castelli I, Castelli II, and Ross, which are hereby incorporated by reference.

As discussed above, the sustained-release formulation of the present invention is suitable for administration to a woman for whom there is reason to believe that she may be pregnant or of a woman who believes that she may soon become pregnant. In this regard, a sustained-release formulation would be regarded as not being "suitable for administration to a woman for whom there is reason to believe that she may be pregnant or of a woman who believes that she may soon become pregnant" if it were to contain biologically active materials or other materials that are recognized as being harmful to pregnant women or fetuses, such as materials that are contraindicated for pregnant women (e.g., methotrexate).

In certain embodiments, the sustained-release formulation of the present invention is substantially free of methotrexate. As used herein, "substantially free of methotrexate" is meant to refer to formulations which contain no methotrexate or, if they do contain methotrexate, the amount of methotrexate contained is less than that which is recognized as being harmful to pregnant women or fetuses.

In certain embodiments, the sustained-release formulation of the present invention contains less than 1 mg (e.g., less than 0.5 mg, less than 0.2 mg, less than 0.1 mg, less than 0.05 mg, less than 0.01 mg, etc.) of methotrexate.

The sustained release formulation can be prepared by any suitable method. For example, the reduced folate, optional folic acid, and optional other actives can be dispersed in a slowly dissolving matrix; or they can be encapsulated in a slowly dissolving matrix (e.g., coated with a slowly dissolving polymer); or they can be encapsulated in a plurality of slowly dissolving matrices (e.g., coated with various polymers having a range of dissolution profiles or coated with varying thicknesses of a slowly dissolving polymer). Further details regarding the preparation of these sustained release formulations can be found, for example, in *Handbook of Pharmaceutical Excipients*, 3rd Edition (2000), American Pharmaceutical Association; *The Theory and Practice of Industrial Pharmacy*, 3rd Edition, Lachman et al. 1986; Pharmaceutical Dosage Forms: Tablets Volume Edition, Christopher T, edition, 1995; and Remington's Pharmaceutical Sciences, 2000; Gaucher et al., "Polymeric Micelles for Oral Drug Delivery," *Eur. J. Pharm. Biopharm.*, 76(2):147-158 (2010); Asane et al., "Polymers for Mucoadhesive Drug Delivery System: A Current Status," *Drug Dev. Ind. Pharm.*, 34(11):1246-1266 (2008); Streubel et al., "Drug Delivery to the Upper Small Intestine Window Using Gastroretentive Technologies," *Curr. Opin. Pharmacol.*, 6(5):501-508 (2006); Pathan et al., "Buccoadhesive Drug Delivery Systems—Extensive Review on Recent Patents," *Recent Pat. Drug Deliv. Formul.*, 2(2):177-188 (2008); Sathish et al., "Floating Drug Delivery Systems for Prolonging Gastric Residence Time: a Review," *Curr. Drug Deliv.*, 8(5):494-510 (2011); Katakam et al., "Floating Drug Delivery Systems: A Review," *Current Trends in Biotechnology and Pharmacy*, 4(2):610-647 (2010); Soni et al., Gastroretentive Drug Delivery Systems: A Review," *International Journal of Pharma World Research*, 2(1):1-24 (January-April 2011), which are hereby incorporated by reference.

As mentioned above, in certain embodiments of the methods of the present invention, commencement of repletion phase dosing can be triggered by becoming aware that the woman is pregnant as the result of a positive pregnancy test. As also mentioned above, repletion phase dosing is preferably commenced as soon as possible after, for example, a positive pregnancy test. The present invention also relates to kits which facilitate such quick commencement of repletion phase dosing.

More particularly, the present invention, in yet another aspect thereof, relates to a kit which includes a pregnancy test device and a repletion dose of folate comprising no less than about 2.5 micromole of folate. In certain embodiments, the kit further includes a second repletion dose of folate comprising no less than about 2.5 micromole of folate. Additional (e.g., a third, a fourth, etc.) repletion doses of folate comprising no less than about 2.5 micromole of folate can also be included.

The pregnancy test device included in the kits of the present invention can be an over-the-counter pregnancy test device. Alternatively, the pregnancy test device can be one which is available only clinically or one which is available only with a prescription. Suitable pregnancy test devices include those which are based on measurement of human chorionic gonadotropin in urine.

Suitable folates for use in the kits of the present invention include those discussed above. For example, the folate can be folic acid or a reduced folate or a polyglutamyl derivative thereof or combinations thereof. Examples of suitable reduced folate are also discussed hereinabove. Illustratively, the reduced folate can be selected from the group consisting of tetrahydrofolic acid, 5-methyl-tetrahydrofolic acid, 5-formyl-tetrahydrofolic acid, 10-formyl-tetrahydrofolic acid, 5,10-methylene-tetrahydrofolic acid, 5,10-methenyl-tetrahydrofolic acid, 5-formimino-tetrahydrofolic acid, 7,8-dihydrofolic acid, and polyglutamyl derivatives thereof.

Illustratively, in certain embodiments, the reduced folate is 5-methyl-tetrahydrofolic acid or a polyglutamyl derivative thereof. By way of further illustration, in certain embodiments, the reduced folate is substantially chirally pure (e.g., greater than 90% chiral purity) 5-methyl-(6S)-tetrahydrofolic acid or a polyglutamyl derivative thereof; while in other embodiments, the reduced folate is racemic 5-methyl-(6)-tetrahydrofolic acid or a polyglutamyl derivative thereof.

Examples of suitable dosage forms and amounts of folate contained in the repletion doses used in the kits of the present invention include those described hereinabove.

The kits of the present invention can further include other biologically active materials, such as those described hereinabove. For example, the kit can further include vitamin B12. Where the kit includes other biologically active materials (e.g., vitamin B12), such other biologically active materials can be packaged separately from the folate, or the two can be packaged together, for example, as where the folate and the other biologically active materials are in a single dosage form. For example, in certain embodiments, the kit further includes vitamin B12, and the repletion dose of folate and the vitamin B12 are contained in a single dosage form.

By way of further illustration, the kits of the present invention can include a pregnancy test device and one or more repletion doses of folate in a sustained-release formulation. For example, suitable sustained release formulations can include a reduced folate and, optionally, folic acid incorporated in a matrix effective to release from about 4 to about 200 micromoles of the reduced folate and optional folic acid over a period of from about 4 hours to about 2 days. Examples of such sustained release formulations are described above. Alternatively, suitable sustained release formulations for inclusion with the kits of the present invention can include folic acid (and no reduced folate) incorporated in a matrix effective to release from about 4 to about 200 micromoles of folic acid over a period of from about 4 hours to about 2 days.

The aforementioned kits of the present invention can also include other materials, such as instructions detailing how and when to use the pregnancy test device, how and when to administer the repletion dose or doses of folate, and the like. Suitable instructions on how and when to administer the repletion dose or doses include those which are consistent with above-described methods of the present invention.

It will be appreciated from the above discussion and the examples which follow that, while the above discussion contemplates the administration of vitamin B12 in conjunction with the administration of folate, administration of vitamin B12 alone (i.e., without folate) can increase plasma B12 levels in a pregnant woman to a degree sufficient to reduce NTD risk associated with B12 deficiency. In view of this, the present invention also relates to methods for increasing and maintaining vitamin B12 levels of a woman for whom there is reason to believe that she may be pregnant or of a woman who believes that she may soon become pregnant by administering to the woman vitamin B12 at a daily dose of at least about 0.2 mg (e.g., of from about 0.2 mg to about 10 mg, of from about 0.25 mg to about 10 mg, of about 0.2 mg, of about 0.25 mg, of about 0.5 mg, of about 1 mg, of about 2 mg, of about 3 mg, of about 5 mg, of about 10 mg, of between about 0.5 and about 3 mg, etc.) for at least 28 days (e.g., for at least 30 days, for at least 35 days, for at least 40 days, etc.).

The present invention is further illustrated by the following non-limiting examples.

EXAMPLES

Example 1—Rapid Elevation of Serum Folate by 5-MTHF, Trial A

A study of the rate of increase of serum folate with 5-methyl-6S-tetrahydrofolate (6S-5-MTHF) was performed with women of child bearing age (final range: 20 to 44 years old). Volunteers were screened for fasting serum folate, and the lower quintile enrolled (n=21 participants). On the first day, a baseline fasting blood sample was obtained using a serum separator tube, and then a 7.5 mg (16.3 micromoles) oral dose of 6S-5-MTHF along with 0.5 mg of cyanocobalamin was administered. After 24 hours (day 2) and again after 48 hours (day 3) fasting blood samples were withdrawn, and the same doses of 6S-5-MTHF and vitamin B12 were administered. At 72 hours (day 4) and 96 hours (day 5), further blood samples were withdrawn, but without administration of vitamins for the first 10 Subjects.

Eleven of the 21 subjects agreed to continue with a daily supplement containing 0.4 mg of folic acid starting on day 4. These subjects returned on days 12 and 19 to provide serum samples. Compliance was established by counting the excess tablets at the end of the study.

The serum samples were frozen and then initially analyzed for total folate using the Immulite 2000 competitive binding assay, and later by microbiological assay using *L. rhamnosus*. Serum B12 was determined using the Immulite 2000 assay. This study and the following trials B and C were performed with approval by the Institutional Review Board of the University of South Alabama.

The total serum folate by microbiological assay in each of the samples is shown in FIG. 1 (solid line). The average concentration was raised from a baseline value of 22.2 nM up to 85.8 nM with just three daily 7.5 mg (16.3 µmol) doses of 6S-5-MTHF. A dose of folate is largely cleared from the plasma after 24 hours, with some portion being excreted into the urine. Therefore, each of the day 2, 3, and 4 blood samples approaches a new homeostatic folate level following the disposition of the previous dose, although by day 5 (48 hours after the last dose) the average total serum folate declined somewhat. Over the next two weeks those subjects who were administered 0.4 mg/d of folic acid reached a new plateau around 55 nM. The 5-MTHF component of the total folate (measured by HPLC with fluorescence detection) was about 43 nM in the final plateau (FIG. 1 dotted line). The rate and extent of the increase in total serum folate observed is unexpected, as is the ability of the subsequent 0.4 mg/d dose of folic acid to maintain a level sufficiently high to reduce the risk for neural tube defects in a developing embryo of most of the women should they have recently become pregnant.

Figure 2:
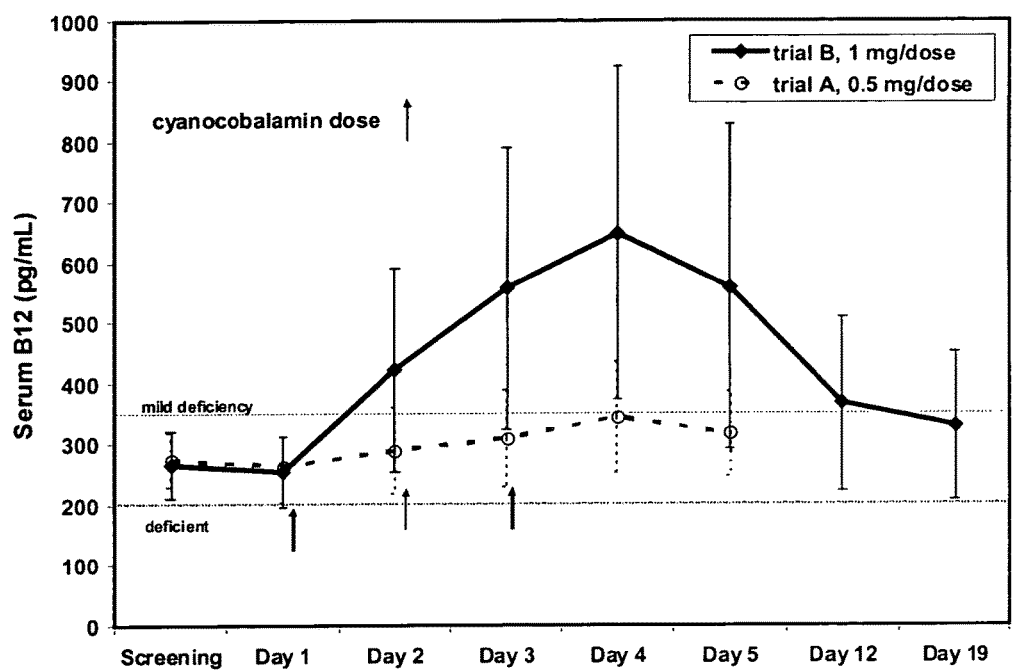
FIG. 2 is a graph showing changes in serum vitamin B12 for subjects receiving 0.5 mg of cyanocobalamin per dose (dotted line) and for subjects receiving 1.0 mg of cyanocobalamin per dose (solid line).

The average vitamin B12 levels specifically for those subjects (n=6) with screening values below 330 pg/mL are shown in FIG. 2 (dotted line). By 72 hours after initiation of the three doses, serum B12 increased on average by about 80 pg/mL, and then fell slightly. Levels below 200 pg/mL are considered to be deficient, and those between 200 and 350 pg/mL are generally considered to be low-normal. Data beyond day 5 are not available for this trial, since only one of those with sub-optimal B12 status volunteered to continue.

Example 2—Rapid Elevation of Serum Folate by 5-MTHF, Trial B

A second trial was performed that was similar to the above trial A (Example 1), except that:
1) five doses of 7.5 mg of 5-methyl-6S-tetrahydrofolate were administered every 12 hours (instead of three doses over 24 hours),
2) three doses of 1.0 mg vitamin B12 were administered on the first three days (instead of three doses of 0.5 mg),
3) all subjects were administered a maintenance dose of 0.8 mg/d 6S-5-MTHF starting 24 hours after the last 7.5 mg dose.

Figure 3:
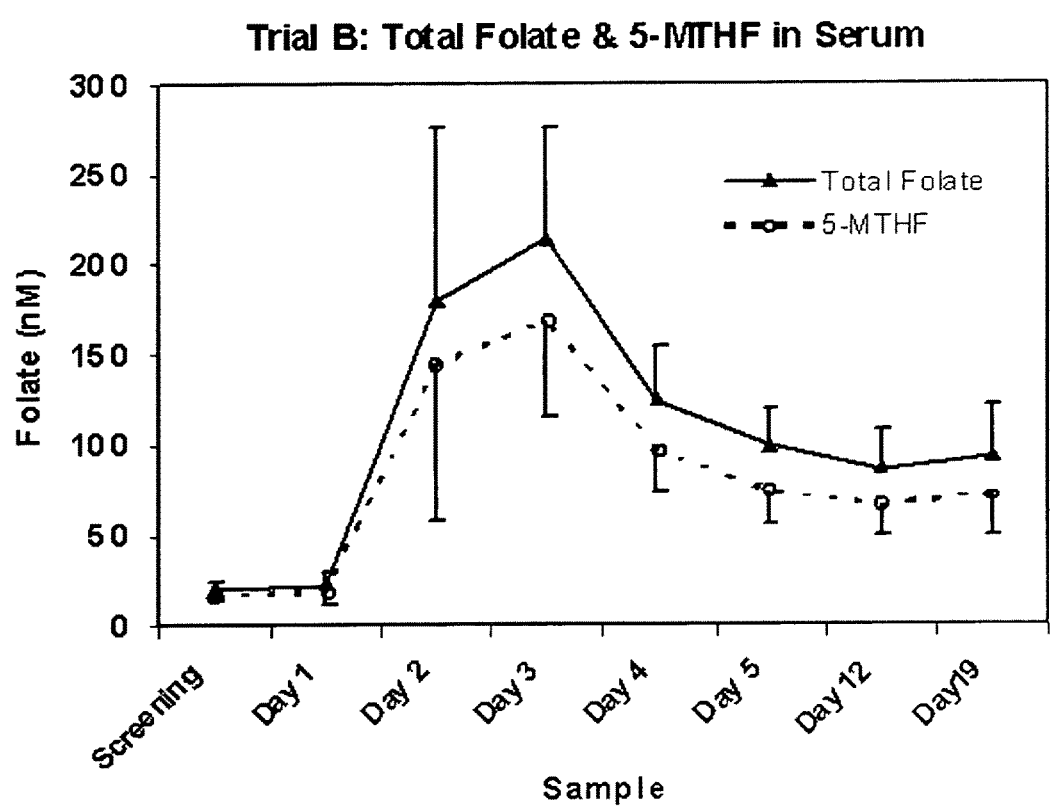
FIG. 3 is a graph showing the results of another study (Trial B) of the rate of increase of serum folate with 5-MTHF administration. The solid line represents total serum folate, and the dotted line represents the 5-MTHF component of the total serum folate.

The 21 volunteers with a value below 25 nM serum folate at screening ranged between 20 to 44 years old. It should be noted that 5-MTHF is the predominate serum/plasma folate typically constituting about 80 to 90% of the total folate. The serum 5-MTHF greatly increased in the day 2 and 3 samples (FIG. 3, dotted line). This is in part due to the twice per day administration, resulting in incomplete clearance after only about 12 hours. However, the day 4 sample averaging 98 nM and the day 5 sample 74 nM, are taken 24 and 48 hours, respectively, after the last 7.5 mg dose. Administration of 0.8 mg/d of 6S-5-MTHF starting on day 4 maintains serum levels at an average higher than 66 nM over the next two weeks. Total folate as determined by microbiological assay is shown by the solid line in FIG. 3; only a single woman was ever below 50 nM (and then only for one measurement) during this study. Considering yet other pharmacokinetic data from our laboratory, this represents the discovery of a method for rapidly increasing and maintaining throughout a critical period of embryonic development a woman's plasma/serum folate levels starting as soon an half hour after administration of the first dose.

The changes in serum B12 are shown in FIG. 2 (solid line). The rate of increase following the three daily 1.0 mg doses cyanocobalamin is considerably greater than observed with the 0.5 mg doses found in the above trial A. By day 4, 88% subjects were in the normal range. Unexpectedly, subsequent to discontinuation of B12 treatment, serum B12 levels fall in an approximate exponential fashion with a half life of about 2½ days. It is believed that this may be due to uptake of the plasma B12 into the tissues of the deficient or mildly deficient subjects. None the less, by day 12 nearly half of the subjects were still in the normal range. These results suggest that the optimal dose of B12 may be higher than three×1.0 mg in the initial phase of treatment, and/or that an elevated dose of B12 beyond that found in typical prenatal vitamins will be useful for maintaining serum/plasma levels during the early period of embryonic development.

Example 3—Rapid Elevation of Serum Folate by Folic Acid

A third trial C was performed that was identical to the above trial A (Example 1), except that 7.5 mg of folic acid was administered every 24 hours for three days instead of 7.5 mg of 5-methyl-6S-tetrahydrofolate.

Administration of 0.5 mg B12, and the administration of 0.4 mg/d of folic acid for maintenance starting day 4 was the same as in Trial A. Twenty women were entered subsequent to screening, and all completed the full length of the trial, except that one subject failed to provide the final sample on day 19.

Figure 4:
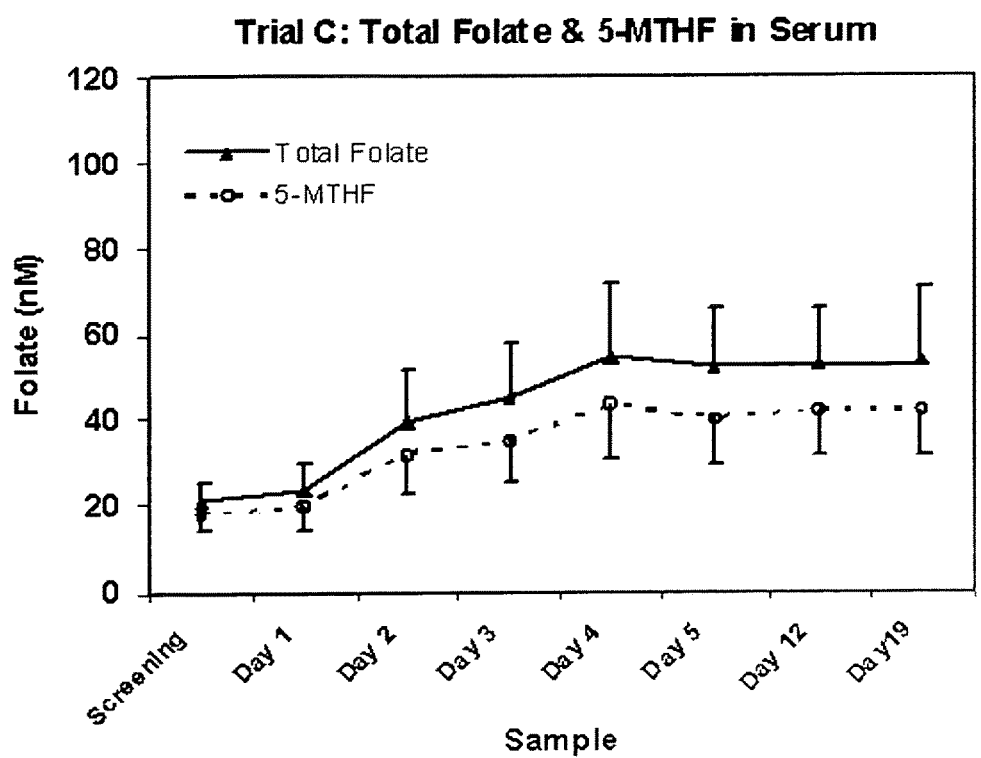
FIG. 4 is a graph showing the results of a study (Trial C) of the rate of increase of serum folate with folic acid administration. The solid line represents total serum folate, and the dotted line represents the 5-MTHF component of the total serum folate.
Figure 5:
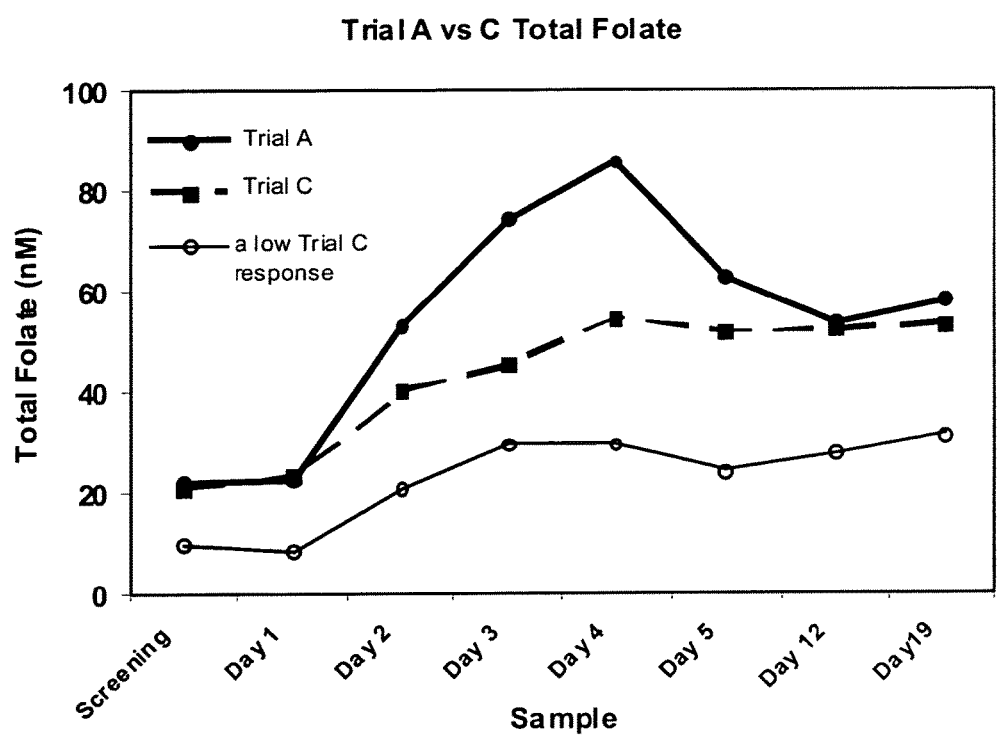
FIG. 5 is a graph comparing the rate of increase of total serum folate with 5-MTHF administration (Trial A) (filled circles, bold solid line) to the rate of increase of total serum folate with folic acid administration (Trial C) (filled squares, bold dashed line).

In this trial with initial high doses of folic acid, although the averages for both total folate by microbiological assay and 5-MTHF assay (see FIG. 4) eventually reached similar values in serum by days 12 and 19 to those in Trial A (see FIG. 5 for comparison), there was a highly significant lag in reaching elevated status with this form of folate. For example, by day 2 whereas the first dose of 5-MTHF in trial A increased average total folate to 53 nM, folic acid only produced an average of 40 nM in serum (P=0.007). This difference persisted out to at least day 5, and was also seen in the measurements of serum 5-MTHF which had even higher statistical significance (data not shown). Especially important is the observation of a sub-population of subjects who responded particularly slowly to folic acid in comparison to 5-MTHF. For example, by the second day, 8 of the 20 (40%) administered folic acid had failed to achieve greater than 37 nM serum total folate, whereas only three (15%) had not reached this level with 5-MTHF in Trial A. By the third day, whereas all of the subjects in Trial A were above 44 nM, 9 of those in Trial C with folic acid were below this level of total folate. By the fourth day, whereas all of the subjects in Trial A were above 55 nM, 10 of those in Trial C with folic acid were below 50 nM total folate. A similar lag in rapidity of repletion with folic acid in comparison to administration of 5-MTHF was observed using the serum 5-MTHF measurements. An example of a subject in Trial C with folic acid is also shown in FIG. 5 for which serum total folate never reached a concentration higher than 32 nM in any measurement. This non-uniformity and delay of serum folate elevation by high dose folic acid is not expected from the literature. Moreover, the clear and more consistent advantage of 5-MTHF over folic acid in this regard is unanticipated. The ability to consistently achieve rapid adequate serum/plasma folate concentrations is important to the minimizing the risk for birth defects occurring early in pregnancy.

Example 4—Use of Rapid Elevation of Serum Folate to Reduce Risk of NTD

The benefits of the present invention (especially with respect to reducing the risk of having an NTD affected birth) are based, in part, upon the sequence and timing of events leading to neural tube closure. During Carnegie stage 7 of embryonic development (between 16 and 17 days post conception) the notochordal process forms from migrating mesenchymal cells which expands cranially between the ectoderm and endoderm. This process is transformed into the notochord by about 18 days post conception. Also, by Carnegie stage 8 (18 to 19 days post conception) the neural plate forms from the ectoderm in coordination with the developing notochord. The neural groove in the plate also appears by this time. The neural folds forming the sides of the groove become further elevated during Carnegie stage 9 (~20 days post conception) when the first somites, which are a major and clear landmark of embryonic development, are formed. During Carnegie stage 10 (21 to 22 days post conception, with between 4 to 10 somite pairs) the neural folds begin to close. This process involves multiple closure sites. The number of sites has been the subject of some debate, but the cranial portion is closed by about 24 to 25 days post conception (Carnegie stage 11). The caudal portion is closed by 26 to 27 days (Carnegie stage 12). Most consider neural tube closure to be totally complete by at the most 28 days post conception.

Nearly all descriptions of defects of human neuralation are in embryos at Carnegie stage 11 and later (Nakatsu et al., "Neural Tube Closure in Humans Initiates at Multiple Sites: Evidence from Human Embryos and Implications for the Pathogenesis of Neural Tube Defects," *Anat. Embryol. (Berl.)*, 201(6):455-466 (2000), which is hereby incorporated by reference. A single example of prosencephalic platyneuria has been described in a stage 10 embryo. There is a single report of duplication of the neural plate at stage 10, though it is not clear that this is a precursor to NTD. The present invention is based, in part, on the realization that achieving adequate folate levels, especially in terms of the plasma levels from which the embryo derives its nutrients, prior to Carnegie stage 10 (~21 days post conception) can aid in preventing folate deficiency related NTD. However, as noted above, women who have conceived miss their menstrual period on average 13 days after conception (with 97.5% occurring within 20 days). Moreover, as also noted above, there are several methods for establishing pregnancy several days prior to a missed menses, such as by measuring hCG in urine or serum.

In view of this, there is a previously unrecognized and unexploited window of opportunity for folate repletion starting as soon as pregnancy is determined or suspected. This window can be very short, and it would be highly advantageous to replete a women within about 3 days. Even if such an opportunity had been recognized, it is widely considered not possible to raise folate levels as quickly as this. This widely-held view is the basis of the uniform consensus that a women of child bearing age should consume 400 µg/d of folate for a period of at least one month prior to attempting conception. Brämswig et al., "Supplementation with a Multivitamin Containing 800 Microg of Folic Acid Shortens the Time to Reach the Preventive Red Blood Cell Folate Concentration in Healthy Women," *Int. J. Vitam. Nutr. Res.*, 79(2):61-70 (2009), found that average plasma folate levels could be elevated to 50 nM and average red cell levels to 919 nM after 4 weeks of administration of 800 µg of folic acid. There is no suggestion or indication in this work that an adequate level of folate could be achieved in a shorter period, let alone in as little as 3 days. Nguyen examined the effect of treatment of women with 1 or 5 mg/day of folic acid, and found that average plasma folate was considerably elevated by 2 weeks. The baseline folate levels of the women in this study was already quite high, and thus not representative of the target population. Again there is no indication that adequate levels would be produced within as little as 3 days with folic acid, especially in folate deficient women. Neither Bramswig et al. nor Nguyen et al. suggest an advantage in the use of high dose of tetrahydrofolate or a one-carbon derivative of tetrahydrofolate. Examples 1-3, hereinabove, demonstrate that the necessary folate levels can be achieved within 2 or 3 days.

The results of the three trials (Examples 1-3) also show, unexpectedly, that it is possible to rapidly replete a folate deficient woman within a few days such that, when switched to a daily dose of folate in an amount near a standard prenatal vitamin, plasma/serum levels can be maintained continuously above a level likely to be protective for birth defects. The ability of a repletion regime to be subsequently maintained with folate within the range of prenatal vitamins has not been previously examined, and, in particular, it has not been studied in folate deficient women of child bearing age. The results of trial A show that many, but not quite all, women in this population can be maintained above the likely protective level using the RDA for folate for non-pregnant adults. It should be noted that in trial A subjects are nearly all above this level during the repletion phase following the second dose at 24 hours. Trial B shows that essentially the entire study group could be well maintained on 0.8 mg/d of folate (the RDA for pregnant women) after having received 5 doses of 16.3 micromoles (7.5 mg) of 6S-5-MTHF administered every 12 hours. Other populations, for example, having a different body mass or racial composition, might respond somewhat differently to the dose regimes used in trials A and B. Comparison of the two trials suggests that it may be important to switch to maintenance dose administration as soon as possible (such as in trial B) after completion of the repletion phase. In addition, the administration of folate in the amount of the RDA for prenatal vitamins may be more effective than the lower amount recommended for non-pregnant adults. Both trials A and B employed 6S-5-MTHF during the rapid repletion phase; had folic acid been used instead, all of the subjects would have been exposed to extremely high unmetabolized folic acid for many hours after each dose. Rapid repletion specifically with high doses of 6S-5-MTHF has not been previously examined. Permanent incorporation of 5-MTHF into cells has been considered to be limited by its poor rate of polyglutamylation. For at least this reason, the ability of this folate form in such doses to elevate folate status in a manner that can then be maintained is would not have been expected.

Spiegelstein et al., "Embryonic Development of Folate Binding Protein-1 (Folbp1) Knockout Mice: Effects of the Chemical Form, Dose, and Timing of Maternal Folate Supplementation," *Dev. Dyn.*, 231(1):221-231 (2004) generated mice homozygous for loss of folate binding protein 1. If untreated, these mice died in utero. If given either 5-formyl-tetrahydrofolate or 5-methyl-tetrahydrofolate some of these mice survived, but were subject to malformations, some of which were NTD. The folate treatment did not entirely prevent malformations, but was optimal when given between days E7-E9. It should be pointed out, however, that defects in the human equivalent of folate binding protein 1 (FR-alpha) have not been shown to contribute significantly to NTD risk. The possibility that autoantibodies against FR-alpha are associated with NTD has proved controversial. In addition, the doses given to the mice ranged between 10.75 to 43.0 micromoles/kg/day. This is much higher than the total dose of 500 micromoles per woman over the entire course of the repletion phase described herein. For a 65 kg (143 lb) woman this is at most 7.5 micromoles per kg over the entire repletion phase, not just per day.

It should be understood that rapid repletion with folate will not in every case prevent neural tube or other birth defects for several reasons among which are: (1) as already described, not all neural tube or other defects are folate responsive; (2) The luteal phase of about 2.5% of women lasts 20 or more days leaving a very brief window of opportunity before the outset of the neural tube closure process; (3) pregnancy test methods, especially some OTC products, can produce a significant rate of false negative results; and (4) additional, as yet unknown, nutrients beyond even vitamin B12 and/or inositol may be required. Despite these factors, the majority of women who quickly start rapid folate repletion described herein within a few days surrounding the date of the next expected menses or a positive hCG test, and who either lack adequate folate levels and/or have risk factors can have a decreased chance for a child affected by birth defects.

Although the invention has been described in detail for the purpose of illustration, it is understood that such detail is solely for that purpose, and variations can be made therein by those skilled in the art without departing from the spirit and scope of the invention which is defined by the claims that are set forth below.

What is claimed is:

1. A method for rapidly repleting folate levels of a woman for whom there is reason to believe that she may be pregnant or of a woman who believes that she may soon become pregnant, said method comprising:
administering to the woman two or more repletion doses of reduced folate during a repletion phase, wherein each of the repletion doses comprises no less than about 2.5 micromole of reduced folate, wherein the repletion doses are administered no more than about one day apart, wherein a total number of repletion doses is administered to the woman, and wherein the total number of repletion doses administered to the woman is 72 or fewer, wherein the repletion phase is carried out for no more than about 12 days, and wherein the reduced folate is selected from the group consisting of 5-methyl-tetrahydrofolic acid, 5-formyl-tetrahydrofolic acid, and polyglutamyl derivatives thereof.

2. A method for rapidly repleting folate levels of a woman for whom there is reason to believe that she may be pregnant or of a woman who believes that she may soon become pregnant, said method comprising:
administering reduced folate to the woman during a repletion phase, wherein a total amount of reduced folate is administered to the woman per day during the repletion phase, wherein the total amount of reduced folate administered to the woman per day during the repletion phase is greater than about 10 micromole and no greater than about 200 micromole, and wherein the repletion phase is carried out for no more than about 12 days, and wherein the reduced folate is selected from the group consisting of 5-methyl-tetrahydrofolic acid, 5-formyl-tetrahydrofolic acid, and polyglutamyl derivatives thereof.

3. A method for rapidly repleting folate levels of a woman for whom there is reason to believe that she may be pregnant or of a woman who believes that she may soon become pregnant, said method comprising:
administering reduced folate to the woman during a repletion phase, wherein an amount of reduced folate is administered per dose, wherein a number of doses is administered per day, wherein the amount of reduced folate administered per dose and the number of doses administered per day are selected such that the woman's minimum plasma folate level does not fall below 35 nM, and wherein the repletion phase is carried out for no more than about 12 days, and wherein the reduced folate is selected from the group consisting of 5-methyl-tetrahydrofolic acid, 5-formyl-tetrahydrofolic acid, and polyglutamyl derivatives thereof.

4. The method according to claim 3, wherein the amount of reduced folate administered per dose and the number of doses administered per day are selected such that the woman's minimum plasma folate level does not fall below 40 nM.

5. The method according to claim 3, wherein the amount of reduced folate administered per dose and the number of doses administered per day during the repletion phase constitutes a daily repletion dose, wherein said method further comprises, subsequent to the repletion phase, administering folate to the woman during a maintenance phase, wherein a total amount of folate is administered to the woman per day during the maintenance phase, and wherein the total amount of folate administered to the woman per day during the maintenance phase is greater than about 0.4 micromole and less than the daily repletion dose.

6. The method according to claim 5, wherein the total amount of folate administered to the woman per day during the maintenance phase is greater than about 0.4 micromole and less than 10 micromole.

7. The method according to claim 5, wherein the total amount of folate administered to the woman per day during the maintenance phase is greater than about 0.4 micromole and less than about 2.5 micromole.

8. The method according to claim 3, wherein the woman is a woman for whom there is reason to believe that she may be pregnant.

9. The method according to claim 8, wherein the repletion phase is commenced within 12 hours of becoming aware that she may be pregnant.

10. The method according to claim 8, wherein the repletion phase is commenced within 1 hour of becoming aware that she may be pregnant.

11. The method according to claim 3, wherein the repletion phase is commenced within 24 hours of the woman having a positive pregnancy test.

12. The method according to claim 3, wherein the repletion phase is commenced within 24 hours of the woman having a positive pregnancy test and wherein a repletion dose of folate is packaged with the pregnancy test.

13. The method according to claim 3, wherein the woman is established as having deficient folate levels; wherein the woman has a history of deficient folate intake from diet or supplements; wherein the woman has one or more risk factors for having a birth affected by neural tube defects, heart defects, orofacial clefts, or combinations thereof.

14. The method according to claim 3, wherein the woman has not previously had a pregnancy affected by neural tube defect or by cleft lip/palate defects.

15. The method according to claim 3, wherein the folate administered to the woman during the maintenance phase is folic acid.

16. The method according to claim 3, wherein the folate administered to the woman during the maintenance phase is a reduced folate or a polyglutamyl derivative thereof.

17. The method according to claim 3, wherein the folate administered to the woman during the maintenance phase is a reduced folate selected from the group consisting of tetrahydrofolic acid, 5-methyl-tetrahydrofolic acid, 5-formyl-tetrahydrofolic acid, 10-formyl-tetrahydrofolic acid, 5,10-methylene-tetrahydrofolic acid, 5,10-methenyl-tetrahydrofolic acid, 5-formimino-tetrahydrofolic acid, 7,8-dihydrofolic acid, and polyglutamyl derivatives thereof.

18. The method according to claim 3, wherein the folate administered to the woman during the maintenance phase is 5-methyl-tetrahydrofolic acid or a polyglutamyl derivative thereof.

19. The method according to claim 3, wherein the reduced folate administered to the woman is substantially chirally pure 5-methyl-(6S)-tetrahydrofolic acid or a polyglutamyl derivative thereof.

20. The method according to claim 3, wherein the method further comprises administering vitamin B12 to the woman during the repletion phase.

21. The method according to claim 20, wherein the reduced folate and vitamin B12 are co-administered in a single dosage form.

22. A method for rapidly repleting folate levels of a woman for whom there is reason to believe that she may be pregnant or of a woman who believes that she may soon become pregnant, said method comprising:
administering to the woman two or more repletion doses comprising reduced folate and, optionally, folic acid, wherein each of the repletion doses comprises no less than about 2.5 micromole of reduced folate and optional folic acid and wherein the repletion doses are administered no more than about one day apart, wherein the reduced folate is selected from the group consisting of 5-methyl-tetrahydrofolic acid, 5-formyl-tetrahydrofolic acid, and polyglutamyl derivatives thereof.

23. A method for rapidly repleting folate levels of a woman for whom there is reason to believe that she may be pregnant or of a woman who believes that she may soon become pregnant, said method comprising:
administering reduced folate and, optionally, folic acid to the woman during a repletion phase, wherein a total amount of reduced folate and optional folic acid is administered to the woman per day during the repletion phase and wherein the total amount of reduced folate and optional folic acid administered to the woman per day during the repletion phase is greater than about 10 micromole and no greater than about 200 micromole, wherein the reduced folate is selected from the group consisting of 5-methyl-tetrahydrofolic acid, 5-formyl-tetrahydrofolic acid, and polyglutamyl derivatives thereof.

24. A sustained-release formulation comprising two or more daily doses of a reduced folate incorporated in a matrix effective to release from about 4 to about 200 micromoles of the reduced folate over a period of from about 4 hours to about 2 days, wherein said sustained-release formulation is suitable for administration to a woman for whom there is reason to believe that she may be pregnant or of a woman who believes that she may soon become pregnant, and wherein the reduced folate is selected from the group consisting of 5-methyl-tetrahydrofolic acid, 5-formyl-tetrahydrofolic acid, and polyglutamyl derivatives thereof.

25. The method according to claim 3, wherein the reduced folate administered to the woman is 5-formyl-tetrahydrofolic acid or a polyglutamyl derivative thereof.

26. The method according to claim 3, wherein the woman is not established as having deficient folate levels.

27. The method according to claim 3, wherein the woman is not established as having a elevated total plasma homocysteine level.

28. The method according to claim 3, wherein, during the repletion phase, the number of doses administered per day is 4 and the amount of the reduced folate administered per dose is between about 3.9 micromole and 15.4 micromole.

29. The method according to claim 3, wherein, during the repletion phase, the number of doses administered per day is 3 and the amount of the reduced folate administered per dose is between about 6 micromole and 23 micromole.

30. The method according to claim 3, wherein, during the repletion phase, the number of doses administered per day is 2 and the amount of the reduced folate administered per dose is between about 8.2 micromole and 32.6 micromole.

31. The method according to claim 3, wherein, during the repletion phase, the number of doses administered per day is 1 and the amount of the reduced folate administered per dose is between about 18.5 micromole and 74 micromole.

32. The method according to claim 3, wherein the method further comprises administering at least one other biologically active material; wherein the reduced folate is provided in a kit which comprises, in addition to the reduced folate, the other biologically active material; and wherein the reduced folate and the other biologically active material are packaged together or are packaged separately.

33. The method according to claim 5, wherein, during the repletion phase, the reduced folate is administered to the woman multiple times per day, and wherein one or more of the repletion doses contain an amount of the reduced folate equal to the total amount of folate that is to be administered per day during the maintenance phase.

34. The method according to claim 33, wherein the total amount of folate administered to the woman per day during the maintenance phase is contained in a single daily maintenance dose, and wherein the repletion and maintenance doses are packaged in a kit.

* * * * *